(12) United States Patent
Miyake et al.

(10) Patent No.: US 10,370,451 B2
(45) Date of Patent: Aug. 6, 2019

(54) PREVENTIVE OR THERAPEUTIC AGENT FOR INFLAMMATORY DISEASE

(71) Applicant: The University of Tokyo, Tokyo (JP)

(72) Inventors: Kensuke Miyake, Tokyo (JP); Atsuo Kanno, Tokyo (JP); Yuji Motoi, Tokyo (JP); Masahiro Onji, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 14/785,844

(22) PCT Filed: Oct. 22, 2013

(86) PCT No.: PCT/JP2013/078631
§ 371 (c)(1),
(2) Date: Mar. 14, 2016

(87) PCT Pub. No.: WO2014/174704
PCT Pub. Date: Oct. 30, 2014

(65) Prior Publication Data
US 2016/0185871 A1 Jun. 30, 2016

(30) Foreign Application Priority Data
Apr. 22, 2013 (JP) ................. 2013-089575

(51) Int. Cl.
| | | |
|---|---|---|
| C07K 16/28 | (2006.01) | |
| A61K 39/395 | (2006.01) | |
| C07K 14/705 | (2006.01) | |
| C07K 14/71 | (2006.01) | |
| A61K 39/00 | (2006.01) | |

(52) U.S. Cl.
CPC ...... *C07K 16/2896* (2013.01); *A61K 39/3955* (2013.01); *A61K 2039/505* (2013.01); *C07K 16/28* (2013.01); *C07K 16/2866* (2013.01); *C07K 2317/33* (2013.01); *C07K 2317/34* (2013.01); *C07K 2317/51* (2013.01); *C07K 2317/515* (2013.01); *C07K 2317/565* (2013.01); *C07K 2317/76* (2013.01)

(58) Field of Classification Search
CPC .......... A61K 39/3955; A61K 2039/505; A61K 39/00; A61K 39/39533; C07K 2317/24; C07K 16/30; C07K 2317/34; C07K 16/18; C07K 16/28; C07K 2317/75; C07K 16/2866; C07K 2316/96; C07K 2317/51; C07K 2317/515; C07K 2317/732; C07K 2317/565
See application file for complete search history.

(56) References Cited

U.S. PATENT DOCUMENTS

2012/0101138 A1 4/2012 Bur et al.
2012/0282276 A1 11/2012 Hogaboam et al.

FOREIGN PATENT DOCUMENTS

| WO | WO 2008/103966 | 8/2008 |
|---|---|---|
| WO | WO 2010/054288 | 5/2010 |
| WO | WO-2012/054862 A2 * | 4/2012 |

OTHER PUBLICATIONS

Brorson et al. (J. Immunol. 163:6694-6701 (1999)).*
Brummell et al. (Biochemistry 32:1180-1187 (1993)).*
Burks et al. (PNAS 94:412-417 (1997)).*
Casset et al (2003. Biochemical and Biophysical Research Communications. 307: 198-205).*
Chen et al (1999. J Mol Biol. 293: 865-881).*
Colman (Research in Immunol. 145:33-36 (1994)).*
DePascalis et al (2002. The Journal of Immunology. 169: 3076-3084).*
Holm et al (2007. Mol Immunology. 44: 1075-1084).*
Jang et al. (Molec. Immunol. 35:1207-1217 (1998)).*
Kobayashi et al. (Protein Engineering 12:879-844 (1999)).*
MacCallum et al (1996. J Mol Biol. 262: 732-745).*
Rudikoff et al, 1982 (Proc Natl Acad Sci USA. vol. 79: 1979-1983).*
Vajdos et al (2002. J Mol Biol. 320: 415-428).*
Wu et al. Therapeutic antibody targeting of individual Notch receptors. Nature 464: 1052-1057, 2010.*
Kanno et al. Essential role for Toll-like receptor 7 (TLR7)-unique cysteines in an intramolecular disulfide bond, proteolytic cleavage and RNA sensing. Int Immunol 25(7): 413-422, Feb. 26, 2013.*
Lloyd et al. Modelling the human immune response: performance of a 10(11) human antibody repertoire against a broad panel of therapeutically relevant antigens. Protein Engineering, Design & Selection 22(3): 159-168, 2009.*
International Search Report for International Application No. PCT/JP2013/078631, dated Jan. 28, 2014, with English translation, 12 pages.
Barrat, F. et al., "Treatment of lupus-prone mice with a dual inhibitor of TLR7 and TLR9 leads to reduction of autoantibody production and amelioration of disease symptoms", Eur. J. Immunol., Dec. 2007, vol. 37, No. 12, pp. 3582-3586.
Barton, G. et al., "Intracellular localization of Toll-like receptor 9 prevents recognition of self DNA but facilitates access to viral DNA", Nature Immunology, Jan. 2006, vol. 7, No. 1, pp. 49-56.
Christensen, S. et al., "Toll-like Receptor 7 and TLR9 Dictate Autoantibody Specificity and Have Opposing Inflammatory and Regulatory Roles in a Murine Model of Lupus", Immunity, Sep. 2006, vol. 26, pp. 417-428.
Ehlers, M. et al., "TLR9/MyD88 signaling is required for class switching to pathogenic IgG2a and 2b autoantibodies in SLE", JEM, The Rockerfeller University Press, Mar. 20, 2006, vol. 203, No. 3, pp. 553-561.
Kanno, A. et al., "Detecting endogenous mouse TLR7 by a monoclonal antibody", Proceedings of the Japanese Society for Immunolog, Nov. 12, 2012, vol. 41, p. 168.

(Continued)

*Primary Examiner* — Bridget E Bunner
(74) *Attorney, Agent, or Firm* — Squire Patton Boggs (US) LLP

(57) ABSTRACT

An object of the present invention is to provide a highly-safe and highly-specific preventive or therapeutic agent for inflammatory diseases targeting a TLR7 or TLR9 molecule. The present invention provides a preventive or therapeutic agent for inflammatory diseases containing an anti-TLR7 antibody or anti-TLR9 antibody.

6 Claims, 11 Drawing Sheets
Specification includes a Sequence Listing.

(56) References Cited

OTHER PUBLICATIONS

Lande, R. et al., "Plasmacytoid dendritic cells sense self-DNA coupled with antimicrobial peptide", Nature, Oct. 4, 2007, vol. 449, pp. 564-569.
Hennessy, Elizabeth J. et al., "Targeting Toll-like receptors: emerging therapeutics," Nature Reviews Drug Discovery, Apr. 2010; vol. 9, No. 4, pp. 293-307.
N.N., "Press Release: Idera Pharmaceuticals Announces Positive Top-Line Results From PHASE2 Trial of IMO-3100 in Patients With Moderateto-Severe Plaque Proriasis," Accessed Jan. 12, 2016 <http://ir.ideraphanna.com/phoenix.zhtml?c=208904&p=irol-newsArticle_print&ID=1768483>.
N.N., R&D Systems, "Human TLR7 Antibody" Oct. 13, 2015.
Barrat, F. et al, "Treatment of lupus-prone mice with a dual inhibitor of TLR7 and TLR9 leads to reduction of autoantibody production and amelioration of disease symptoms", Eur J Immunol. Dec. 2007; 37(12): 3582-3586.
Barrat, F. and R. Coffman, "Development of TLR inhibitors for the treatment of autoimmune diseases", Immunol Rev. Jun. 2008; 223: 271-283.
Hari, A. et al, "Toll-Like Receptors: Role in Dermatological Disease", Mediators Inflamm. Aug. 2010; 17 pages.
Cognasse et al., "Identification of two subpopulations of purified human blood B cells, $CD27^-$ $CD23^+$ and $CD27^{high}$ $CD80^+$, that strongly express cell surface Toll-like receptor 9 and secrete high levels of interleukin-6", Immunology. Nov. 2008; 125(3): 430-437. Epub Apr. 28, 2008.
Mortaz et al., "Cigarette smoke induces the release of CXCL-8 from human bronchial epithelial cells via TLRs and induction of the inflammasome", Biochim Biophys Acta. Sep. 2011; 1812(9): 1104-1110. Epub Jun. 12, 2011.
Mouchess et al., "Transmembrane Mutations in Toll-like Receptor 9 Bypass the Requirement for Ectodomain Proteolysis and Induce Fatal Inflammation", Immunity. Nov. 23, 2011; 35(5): 721-732. Epub Nov. 10, 2011.
Schneberger et al, "Expression of Toll-like receptor 9 in mouse and human lungs", J Anat. May 2013; 222(5): 495-503. Epub Mar. 22, 2013.
TLR (Toll-Like Receptor). Datasheet [online]. IMGENEX, Funakoshi News, May 1, 2010, p. 19. Retrieved from the Internet: <URL: http://www.funakoshi.co.jp/>, 2 pages.

* cited by examiner

FIG. 7B
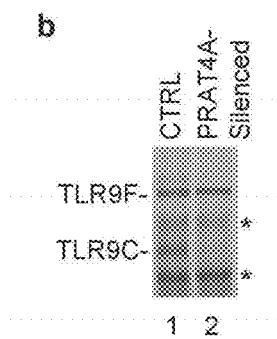
FIG. 7C
```
                          461        467
                           ▼          ▼
Mouse  ADPHPAPLS  TPASKN  FMDRC
       D  PAP+    TP+S++  F    C
Human  GDLAPAPVD  TPSSED  FRPNC
```
FIG. 7D
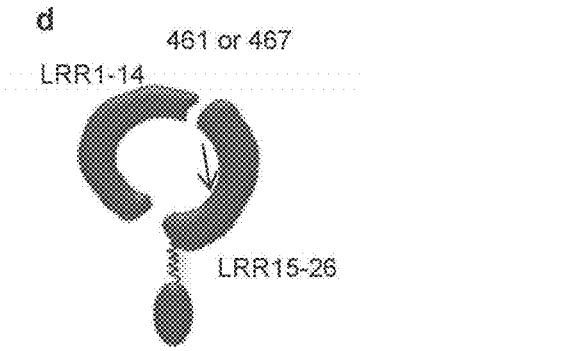
FIG. 7E
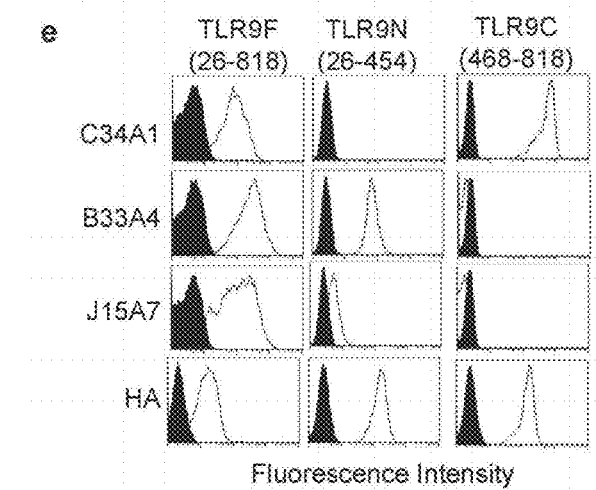

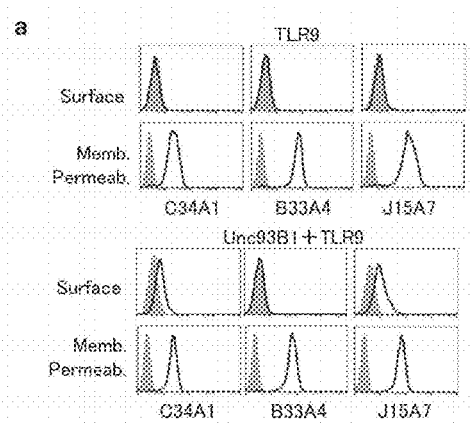
FIG. 8A
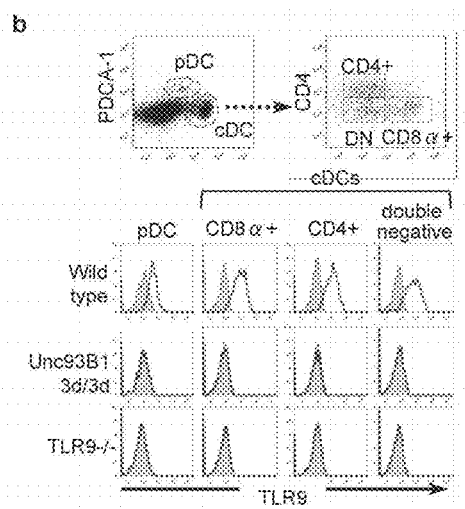
FIG. 8B
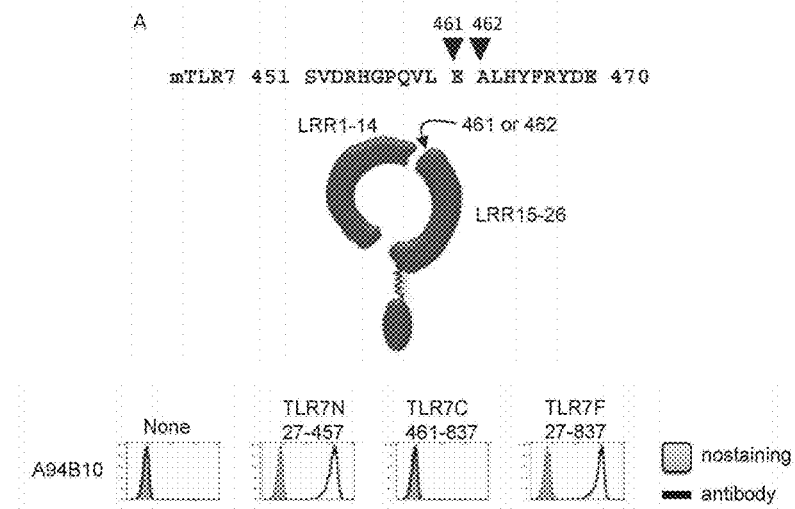
FIG. 9A
FIG. 9B

FIG. 13    The epitope of TLR7 mAbs
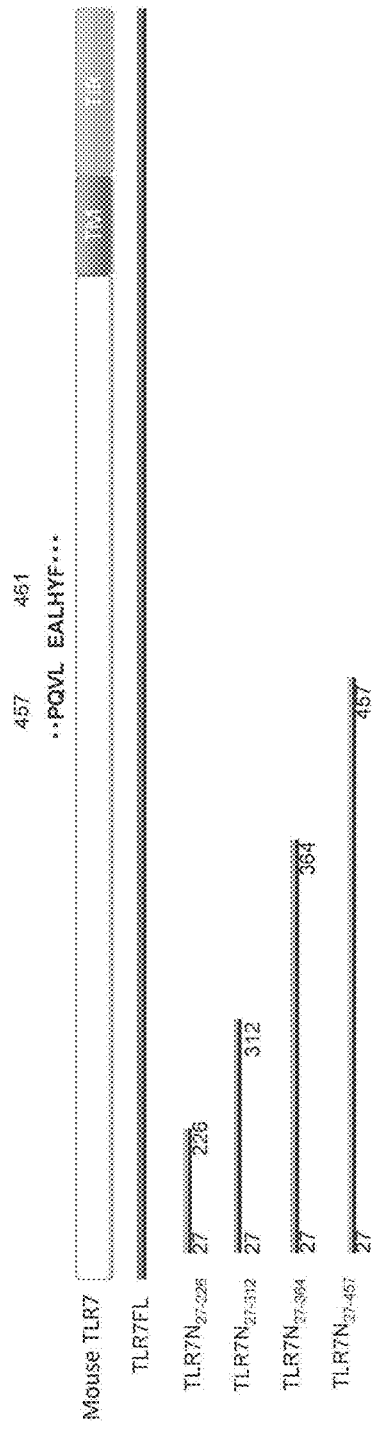
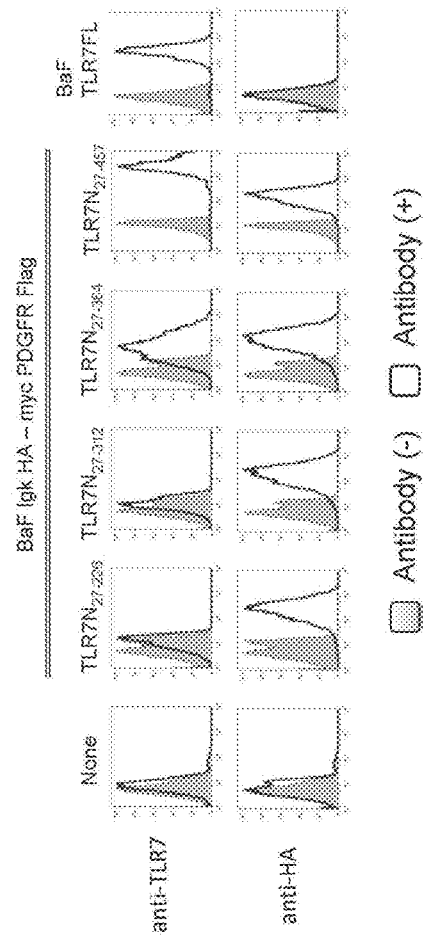

SEQUENCE LISTING

```
<160> NUMBER OF SEQ ID NOS: 43

<210> SEQ ID NO 1
<211> LENGTH: 1050
<212> TYPE: PRT
<213> ORGANISM: Mus musculus
<220> FEATURE:
<221> NAME/KEY: MISC_FEATURE
<223> OTHER INFORMATION: Amino acid sequence of mouse TLR7.

<400> SEQUENCE: 1

Met Val Phe Ser Met Trp Thr Arg Lys Arg Gln Ile Leu Ile Phe Leu
1               5                   10                  15

Asn Met Leu Leu Val Ser Arg Val Phe Gly Phe Arg Trp Phe Pro Lys
            20                  25                  30

Thr Leu Pro Cys Glu Val Lys Val Asn Ile Pro Glu Ala His Val Ile
        35                  40                  45

Val Asp Cys Thr Asp Lys His Leu Thr Glu Ile Pro Glu Gly Ile Pro
    50                  55                  60

Thr Asn Thr Thr Asn Leu Thr Leu Thr Ile Asn His Ile Pro Ser Ile
65                  70                  75                  80

Ser Pro Asp Ser Phe Arg Arg Leu Asn His Leu Glu Glu Ile Asp Leu
                85                  90                  95

Arg Cys Asn Cys Val Pro Val Leu Leu Gly Ser Lys Ala Asn Val Cys
                100                 105                 110

Thr Lys Arg Leu Gln Ile Arg Pro Gly Ser Phe Ser Gly Leu Ser Asp
            115                 120                 125

Leu Lys Ala Leu Tyr Leu Asp Gly Asn Gln Leu Leu Glu Ile Pro Gln
        130                 135                 140

Asp Leu Pro Ser Ser Leu His Leu Leu Ser Leu Glu Ala Asn Asn Ile
145                 150                 155                 160

Phe Ser Ile Thr Lys Glu Asn Leu Thr Glu Leu Val Asn Ile Glu Thr
                165                 170                 175

Leu Tyr Leu Gly Gln Asn Cys Tyr Tyr Arg Asn Pro Cys Asn Val Ser
                180                 185                 190

Tyr Ser Ile Glu Lys Asp Ala Phe Leu Val Met Arg Asn Leu Lys Val
```

-continued

```
                195                 200                 205
Leu Ser Leu Lys Asp Asn Asn Val Thr Ala Val Pro Thr Thr Leu Pro
    210                 215                 220
Pro Asn Leu Leu Glu Leu Tyr Leu Tyr Asn Asn Ile Ile Lys Lys Ile
225                 230                 235                 240
Gln Glu Asn Asp Phe Asn Asn Leu Asn Glu Leu Gln Val Leu Asp Leu
                245                 250                 255
Ser Gly Asn Cys Pro Arg Cys Tyr Asn Val Pro Tyr Pro Cys Thr Pro
                260                 265                 270
Cys Glu Asn Asn Ser Pro Leu Gln Ile His Asp Asn Ala Phe Asn Ser
                275                 280                 285
Leu Thr Glu Leu Lys Val Leu Arg Leu His Ser Asn Ser Leu Gln His
    290                 295                 300
Val Pro Pro Thr Trp Phe Lys Asn Met Arg Asn Leu Gln Glu Leu Asp
305                 310                 315                 320
Leu Ser Gln Asn Tyr Leu Ala Arg Glu Ile Glu Glu Ala Lys Phe Leu
                325                 330                 335
His Phe Leu Pro Asn Leu Val Glu Leu Asp Phe Ser Phe Asn Tyr Glu
                340                 345                 350
Leu Gln Val Tyr His Ala Ser Ile Thr Leu Pro His Ser Leu Ser Ser
                355                 360                 365
Leu Glu Asn Leu Lys Ile Leu Arg Val Lys Gly Tyr Val Phe Lys Glu
    370                 375                 380
Leu Lys Asn Ser Ser Leu Ser Val Leu His Lys Leu Pro Arg Leu Glu
385                 390                 395                 400
Val Leu Asp Leu Gly Thr Asn Phe Ile Lys Ile Ala Asp Leu Asn Ile
                405                 410                 415
Phe Lys His Phe Glu Asn Leu Lys Leu Ile Asp Leu Ser Val Asn Lys
                420                 425                 430
Ile Ser Pro Ser Glu Glu Ser Arg Glu Val Gly Phe Cys Pro Asn Ala
    435                 440                 445
Gln Thr Ser Val Asp Arg His Gly Pro Gln Val Leu Glu Ala Leu His
    450                 455                 460
Tyr Phe Arg Tyr Asp Glu Tyr Ala Arg Ser Cys Arg Phe Lys Asn Lys
465                 470                 475                 480
Glu Pro Pro Ser Phe Leu Pro Leu Asn Ala Asp Cys His Ile Tyr Gly
                485                 490                 495
Gln Thr Leu Asp Leu Ser Arg Asn Asn Ile Phe Phe Ile Lys Pro Ser
                500                 505                 510
Asp Phe Gln His Leu Ser Phe Leu Lys Cys Leu Asn Leu Ser Gly Asn
                515                 520                 525
Thr Ile Gly Gln Thr Leu Asn Gly Ser Glu Leu Trp Pro Leu Arg Glu
    530                 535                 540
Leu Arg Tyr Leu Asp Phe Ser Asn Asn Arg Leu Asp Leu Leu Tyr Ser
545                 550                 555                 560
Thr Ala Phe Glu Glu Leu Gln Ser Leu Glu Val Leu Asp Leu Ser Ser
                565                 570                 575
Asn Ser His Tyr Phe Gln Ala Glu Gly Ile Thr His Met Leu Asn Phe
                580                 585                 590
Thr Lys Lys Leu Arg Leu Leu Asp Lys Leu Met Met Asn Asp Asn Asp
                595                 600                 605
Ile Ser Thr Ser Ala Ser Arg Thr Met Glu Ser Asp Ser Leu Arg Ile
    610                 615                 620
```

-continued

```
Leu Glu Phe Arg Gly Asn His Leu Asp Val Leu Trp Arg Ala Gly Asp
625                 630                 635                 640

Asn Arg Tyr Leu Asp Phe Phe Lys Asn Leu Phe Asn Leu Glu Val Leu
                645                 650                 655

Asp Ile Ser Arg Asn Ser Leu Asn Ser Leu Pro Pro Glu Val Phe Glu
            660                 665                 670

Gly Met Pro Pro Asn Leu Lys Asn Leu Ser Leu Ala Lys Asn Gly Leu
        675                 680                 685

Lys Ser Phe Phe Trp Asp Arg Leu Gln Leu Leu Lys His Leu Glu Ile
690                 695                 700

Leu Asp Leu Ser His Asn Gln Leu Thr Lys Val Pro Glu Arg Leu Ala
705                 710                 715                 720

Asn Cys Ser Lys Ser Leu Thr Thr Leu Ile Leu Lys His Asn Gln Ile
                725                 730                 735

Arg Gln Leu Thr Lys Tyr Phe Leu Glu Asp Ala Leu Gln Leu Arg Tyr
            740                 745                 750

Leu Asp Ile Ser Ser Asn Lys Ile Gln Val Ile Gln Lys Thr Ser Phe
        755                 760                 765

Pro Glu Asn Val Leu Asn Asn Leu Glu Met Leu Val Leu His His Asn
770                 775                 780

Arg Phe Leu Cys Asn Cys Asp Ala Val Trp Phe Val Trp Trp Val Asn
785                 790                 795                 800

His Thr Asp Val Thr Ile Pro Tyr Leu Ala Thr Asp Val Thr Cys Val
                805                 810                 815

Gly Pro Gly Ala His Lys Gly Gln Ser Val Ile Ser Leu Asp Leu Tyr
            820                 825                 830

Thr Cys Glu Leu Asp Leu Thr Asn Leu Ile Leu Phe Ser Val Ser Ile
        835                 840                 845

Ser Ser Val Leu Phe Leu Met Val Val Met Thr Thr Ser His Leu Phe
850                 855                 860

Phe Trp Asp Met Trp Tyr Ile Tyr Tyr Phe Trp Lys Ala Lys Ile Lys
865                 870                 875                 880

Gly Tyr Gln His Leu Gln Ser Met Glu Ser Cys Tyr Asp Ala Phe Ile
                885                 890                 895

Val Tyr Asp Thr Lys Asn Ser Ala Val Thr Glu Trp Val Leu Gln Glu
            900                 905                 910

Leu Val Ala Lys Leu Glu Asp Pro Arg Glu Lys His Phe Asn Leu Cys
        915                 920                 925

Leu Glu Glu Arg Asp Trp Leu Pro Gly Gln Pro Val Leu Glu Asn Leu
930                 935                 940

Ser Gln Ser Ile Gln Leu Ser Lys Lys Thr Val Phe Val Met Thr Gln
945                 950                 955                 960

Lys Tyr Ala Lys Thr Glu Ser Phe Lys Met Ala Phe Tyr Leu Ser His
                965                 970                 975

Gln Arg Leu Leu Asp Glu Lys Val Asp Val Ile Ile Leu Ile Phe Leu
            980                 985                 990

Glu Lys Pro Leu Gln Lys Ser Lys Phe Leu Gln Leu Arg Lys Arg Leu
        995                 1000                1005

Cys Arg Ser Ser Val Leu Glu Trp Pro Ala Asn Pro Gln Ala His
    1010                1015                1020

Pro Tyr Phe Trp Gln Cys Leu Lys Asn Ala Leu Thr Thr Asp Asn
    1025                1030                1035
```

His Val Ala Tyr Ser Gln Met Phe Lys Glu Thr Val
    1040                1045                1050

<210> SEQ ID NO 2
<211> LENGTH: 1032
<212> TYPE: PRT
<213> ORGANISM: Mus musculus
<220> FEATURE:
<221> NAME/KEY: MISC_FEATURE
<223> OTHER INFORMATION: Amino acid sequence of mouse TLR9.

<400> SEQUENCE: 2

Met Val Leu Arg Arg Arg Thr Leu His Pro Leu Ser Leu Leu Val Gln
1               5                   10                  15

Ala Ala Val Leu Ala Glu Thr Leu Ala Leu Gly Thr Leu Pro Ala Phe
            20                  25                  30

Leu Pro Cys Glu Leu Lys Pro His Gly Leu Val Asp Cys Asn Trp Leu
        35                  40                  45

Phe Leu Lys Ser Val Pro Arg Phe Ser Ala Ala Ser Cys Ser Asn
    50                  55                  60

Ile Thr Arg Leu Ser Leu Ile Ser Asn Arg Ile His His Leu His Asn
65                  70                  75                  80

Ser Asp Phe Val His Leu Ser Asn Leu Arg Gln Leu Asn Leu Lys Trp
                85                  90                  95

Asn Cys Pro Pro Thr Gly Leu Ser Pro Leu His Phe Ser Cys His Met
            100                 105                 110

Thr Ile Glu Pro Arg Thr Phe Leu Ala Met Arg Thr Leu Glu Glu Leu
        115                 120                 125

Asn Leu Ser Tyr Asn Gly Ile Thr Thr Val Pro Arg Leu Pro Ser Ser
    130                 135                 140

Leu Val Asn Leu Ser Leu Ser His Thr Asn Ile Leu Val Leu Asp Ala
145                 150                 155                 160

Asn Ser Leu Ala Gly Leu Tyr Ser Leu Arg Val Leu Phe Met Asp Gly
                165                 170                 175

Asn Cys Tyr Tyr Lys Asn Pro Cys Thr Gly Ala Val Lys Val Thr Pro
            180                 185                 190

Gly Ala Leu Leu Gly Leu Ser Asn Leu Thr His Leu Ser Leu Lys Tyr
        195                 200                 205

Asn Asn Leu Thr Lys Val Pro Arg Gln Leu Pro Pro Ser Leu Glu Tyr
    210                 215                 220

Leu Leu Val Ser Tyr Asn Leu Ile Val Lys Leu Gly Pro Glu Asp Leu
225                 230                 235                 240

Ala Asn Leu Thr Ser Leu Arg Val Leu Asp Val Gly Gly Asn Cys Arg
                245                 250                 255

Arg Cys Asp His Ala Pro Asn Pro Cys Ile Glu Cys Gly Gln Lys Ser
            260                 265                 270

Leu His Leu His Pro Glu Thr Phe His His Leu Ser His Leu Glu Gly
        275                 280                 285

Leu Val Leu Lys Asp Ser Ser Leu His Thr Leu Asn Ser Ser Trp Phe
    290                 295                 300

Gln Gly Leu Val Asn Leu Ser Val Leu Asp Leu Ser Glu Asn Phe Leu
305                 310                 315                 320

Tyr Glu Ser Ile Thr His Thr Asn Ala Phe Gln Asn Leu Thr Arg Leu
                325                 330                 335

Arg Lys Leu Asn Leu Ser Phe Asn Tyr Arg Lys Lys Val Ser Phe Ala
            340                 345                 350

```
Arg Leu His Leu Ala Ser Ser Phe Lys Asn Leu Val Ser Leu Gln Glu
            355                 360                 365

Leu Asn Met Asn Gly Ile Phe Phe Arg Leu Leu Asn Lys Tyr Thr Leu
    370                 375                 380

Arg Trp Leu Ala Asp Leu Pro Lys Leu His Thr Leu His Leu Gln Met
385                 390                 395                 400

Asn Phe Ile Asn Gln Ala Gln Leu Ser Ile Phe Gly Thr Phe Arg Ala
                405                 410                 415

Leu Arg Phe Val Asp Leu Ser Asp Asn Arg Ile Ser Gly Pro Ser Thr
                420                 425                 430

Leu Ser Glu Ala Thr Pro Glu Glu Ala Asp Ala Glu Gln Glu Glu
            435                 440                 445

Leu Leu Ser Ala Asp Pro His Pro Ala Pro Leu Ser Thr Pro Ala Ser
            450                 455                 460

Lys Asn Phe Met Asp Arg Cys Lys Asn Phe Lys Phe Thr Met Asp Leu
465                 470                 475                 480

Ser Arg Asn Asn Leu Val Thr Ile Lys Pro Glu Met Phe Val Asn Leu
                485                 490                 495

Ser Arg Leu Gln Cys Leu Ser Leu Ser His Asn Ser Ile Ala Gln Ala
            500                 505                 510

Val Asn Gly Ser Gln Phe Leu Pro Leu Thr Asn Leu Gln Val Leu Asp
            515                 520                 525

Leu Ser His Asn Lys Leu Asp Leu Tyr His Trp Lys Ser Phe Ser Glu
            530                 535                 540

Leu Pro Gln Leu Gln Ala Leu Asp Leu Ser Tyr Asn Ser Gln Pro Phe
545                 550                 555                 560

Ser Met Lys Gly Ile Gly His Asn Phe Ser Phe Val Thr His Leu Ser
                565                 570                 575

Met Leu Gln Ser Leu Ser Leu Ala His Asn Asp Ile His Thr Arg Val
            580                 585                 590

Ser Ser His Leu Asn Ser Asn Ser Val Arg Phe Leu Asp Phe Ser Gly
            595                 600                 605

Asn Gly Met Gly Arg Met Trp Asp Glu Gly Gly Leu Tyr Leu His Phe
            610                 615                 620

Phe Gln Gly Leu Ser Gly Leu Leu Lys Leu Asp Leu Ser Gln Asn Asn
625                 630                 635                 640

Leu His Ile Leu Arg Pro Gln Asn Leu Asp Asn Leu Pro Lys Ser Leu
                645                 650                 655

Lys Leu Leu Ser Leu Arg Asp Asn Tyr Leu Ser Phe Phe Asn Trp Thr
            660                 665                 670

Ser Leu Ser Phe Leu Pro Asn Leu Glu Val Leu Asp Leu Ala Gly Asn
            675                 680                 685

Gln Leu Lys Ala Leu Thr Asn Gly Thr Leu Pro Asn Gly Thr Leu Leu
            690                 695                 700

Gln Lys Leu Asp Val Ser Ser Asn Ser Ile Val Ser Val Val Pro Ala
705                 710                 715                 720

Phe Phe Ala Leu Ala Val Glu Leu Lys Glu Val Asn Leu Ser His Asn
                725                 730                 735

Ile Leu Lys Thr Val Asp Arg Ser Trp Phe Gly Pro Ile Val Met Asn
                740                 745                 750

Leu Thr Val Leu Asp Val Arg Ser Asn Pro Leu His Cys Ala Cys Gly
            755                 760                 765
```

```
Ala Ala Phe Val Asp Leu Leu Leu Glu Val Gln Thr Lys Val Pro Gly
770                 775                 780

Leu Ala Asn Gly Val Lys Cys Gly Ser Pro Gln Leu Gln Gly Arg
785                 790                 795                 800

Ser Ile Phe Ala Gln Asp Leu Arg Leu Cys Leu Asp Glu Val Leu Ser
                805                 810                 815

Trp Asp Cys Phe Gly Leu Ser Leu Leu Ala Val Ala Val Gly Met Val
                820                 825                 830

Val Pro Ile Leu His His Leu Cys Gly Trp Asp Val Trp Tyr Cys Phe
                835                 840                 845

His Leu Cys Leu Ala Trp Leu Pro Leu Leu Ala Arg Ser Arg Arg Ser
850                 855                 860

Ala Gln Thr Leu Pro Tyr Asp Ala Phe Val Val Phe Asp Lys Ala Gln
865                 870                 875                 880

Ser Ala Val Ala Asp Trp Val Tyr Asn Glu Leu Arg Val Arg Leu Glu
                885                 890                 895

Glu Arg Arg Gly Arg Arg Ala Leu Arg Leu Cys Leu Glu Asp Arg Asp
                900                 905                 910

Trp Leu Pro Gly Gln Thr Leu Phe Glu Asn Leu Trp Ala Ser Ile Tyr
                915                 920                 925

Gly Ser Arg Lys Thr Leu Phe Val Leu Ala His Thr Asp Arg Val Ser
930                 935                 940

Gly Leu Leu Arg Thr Ser Phe Leu Leu Ala Gln Gln Arg Leu Leu Glu
945                 950                 955                 960

Asp Arg Lys Asp Val Val Val Leu Val Ile Leu Arg Pro Asp Ala His
                965                 970                 975

Arg Ser Arg Tyr Val Arg Leu Arg Gln Arg Leu Cys Arg Gln Ser Val
                980                 985                 990

Leu Phe Trp Pro Gln Gln Pro Asn  Gly Gln Gly Gly Phe  Trp Ala Gln
        995             1000                1005

Leu Ser  Thr Ala Leu Thr Arg  Asp Asn Arg His Phe  Tyr Asn Gln
    1010                1015                1020

Asn Phe  Cys Arg Gly Pro Thr  Ala Glu
1025                1030

<210> SEQ ID NO 3
<211> LENGTH: 6
<212> TYPE: PRT
<213> ORGANISM: Artificial
<220> FEATURE:
<223> OTHER INFORMATION: Amino acid sequence of heavy chain CDR1 of
      A94B10 antibody.

<400> SEQUENCE: 3

Ser Asp Phe Tyr Met Glu
1               5

<210> SEQ ID NO 4
<211> LENGTH: 19
<212> TYPE: PRT
<213> ORGANISM: Artificial
<220> FEATURE:
<223> OTHER INFORMATION: Amino acid sequence of heavy chain CDR2 of
      A94B10 antibody.

<400> SEQUENCE: 4

Ala Ser Arg Asn Lys Arg Asn Asp His Thr Thr Glu Tyr Ser Ala Ser
1               5                   10                  15
```

Val Lys Gly

<210> SEQ ID NO 5
<211> LENGTH: 11
<212> TYPE: PRT
<213> ORGANISM: Artificial
<220> FEATURE:
<223> OTHER INFORMATION: Amino acid sequence of heavy chain CDR3 of
      A94B10 antibody.

<400> SEQUENCE: 5

Arg Asp Ala Asp Tyr Tyr Gly Ser Ser Thr Trp
1               5                   10

<210> SEQ ID NO 6
<211> LENGTH: 11
<212> TYPE: PRT
<213> ORGANISM: Artificial
<220> FEATURE:
<223> OTHER INFORMATION: Amino acid sequence of light chain CDR1 of
      A94B10 antibody.

<400> SEQUENCE: 6

Lys Ala Ser Gln Asp Val Arg Thr Ala Val Ala
1               5                   10

<210> SEQ ID NO 7
<211> LENGTH: 7
<212> TYPE: PRT
<213> ORGANISM: Artificial
<220> FEATURE:
<223> OTHER INFORMATION: Amino acid sequence of light chain CDR2 of
      A94B10 antibody.

<400> SEQUENCE: 7

Trp Ala Ser Thr Arg His Thr
1               5

<210> SEQ ID NO 8
<211> LENGTH: 8
<212> TYPE: PRT
<213> ORGANISM: Artificial
<220> FEATURE:
<223> OTHER INFORMATION: Amino acid sequence of light chain CDR3 of
      A94B10 antibody.

<400> SEQUENCE: 8

Gln Gln His Tyr Asn Thr Pro Pro
1               5

<210> SEQ ID NO 9
<211> LENGTH: 468
<212> TYPE: PRT
<213> ORGANISM: Artificial
<220> FEATURE:
<223> OTHER INFORMATION: Amino acid sequence of heavy chain of A94B10
      antibody.

<400> SEQUENCE: 9

Met Lys Leu Trp Leu Asn Trp Val Phe Leu Leu Thr Leu Leu His Gly
1               5                   10                  15

Asn Gln Cys Glu Val Lys Leu Val Glu Ser Gly Gly Gly Leu Val Gln
                20                  25                  30

Pro Gly Gly Ser Leu Arg Leu Ser Cys Thr Thr Ser Gly Phe Thr Phe
            35                  40                  45

Ser Asp Phe Tyr Met Glu Trp Val Arg Gln Pro Pro Gly Lys Arg Leu

```
            50                  55                  60
Glu Trp Ile Ala Ala Ser Arg Asn Lys Arg Asn Asp His Thr Thr Glu
65                  70                  75                  80

Tyr Ser Ala Ser Val Lys Gly Arg Phe Ile Val Ser Arg Asp Thr Ser
                85                  90                  95

Gln Asn Ile Leu Tyr Leu Gln Met Asn Ala Leu Arg Ala Glu Asp Thr
                100                 105                 110

Ala Ile Tyr Tyr Cys Ala Arg Asp Ala Asp Tyr Tyr Gly Ser Ser Thr
            115                 120                 125

Trp Tyr Phe Asp Val Trp Gly Ala Gly Thr Thr Val Thr Val Ser Ser
        130                 135                 140

Ala Lys Thr Thr Pro Pro Ser Val Tyr Pro Leu Ala Pro Gly Ser Ala
145                 150                 155                 160

Ala Gln Thr Asn Ser Met Val Thr Leu Gly Cys Leu Val Lys Gly Tyr
                165                 170                 175

Phe Pro Glu Pro Val Thr Val Thr Trp Asn Ser Gly Ser Leu Ser Ser
                180                 185                 190

Gly Val His Thr Phe Pro Ala Val Leu Gln Ser Asp Leu Tyr Thr Leu
            195                 200                 205

Ser Ser Ser Val Thr Val Pro Ser Ser Thr Trp Pro Ser Glu Thr Val
210                 215                 220

Thr Cys Asn Val Ala His Pro Ala Ser Ser Thr Lys Val Asp Lys Lys
225                 230                 235                 240

Ile Val Pro Arg Asp Cys Gly Cys Lys Pro Cys Ile Cys Thr Val Pro
                245                 250                 255

Glu Val Ser Ser Val Phe Ile Phe Pro Pro Lys Pro Lys Asp Val Leu
                260                 265                 270

Thr Ile Thr Leu Thr Pro Lys Val Thr Cys Val Val Val Asp Ile Ser
            275                 280                 285

Lys Asp Asp Pro Glu Val Gln Phe Ser Trp Phe Val Asp Asp Val Glu
        290                 295                 300

Val His Thr Ala Gln Thr Gln Pro Arg Glu Glu Gln Phe Asn Ser Thr
305                 310                 315                 320

Phe Arg Ser Val Ser Glu Leu Pro Ile Met His Gln Asp Trp Leu Asn
                325                 330                 335

Gly Lys Glu Phe Lys Cys Arg Val Asn Ser Ala Ala Phe Pro Ala Pro
                340                 345                 350

Ile Glu Lys Thr Ile Ser Lys Thr Lys Gly Arg Pro Lys Ala Pro Gln
            355                 360                 365

Val Tyr Thr Ile Pro Pro Pro Lys Glu Gln Met Ala Lys Asp Lys Val
        370                 375                 380

Ser Leu Thr Cys Met Ile Thr Asp Phe Phe Pro Glu Asp Ile Thr Val
385                 390                 395                 400

Glu Trp Gln Trp Asn Gly Gln Pro Ala Glu Asn Tyr Lys Asn Thr Gln
                405                 410                 415

Pro Ile Met Asn Thr Asn Gly Ser Tyr Phe Val Tyr Ser Lys Leu Asn
                420                 425                 430

Val Gln Lys Ser Asn Trp Glu Ala Gly Asn Thr Phe Thr Cys Ser Val
            435                 440                 445

Leu His Glu Gly Leu His Asn His His Thr Glu Lys Ser Leu Ser His
        450                 455                 460

Ser Pro Gly Lys
465
```

<210> SEQ ID NO 10
<211> LENGTH: 238
<212> TYPE: PRT
<213> ORGANISM: Artificial
<220> FEATURE:
<223> OTHER INFORMATION: Amino acid sequence of light chain of A94B10
      antibody.

<400> SEQUENCE: 10

Met Gly Ile Lys Met Glu Ser Gln Ile Gln Ala Phe Val Phe Val Phe
1               5                   10                  15

Leu Trp Leu Ser Gly Val Asp Gly Asp Ile Val Met Thr Gln Ser His
            20                  25                  30

Lys Phe Met Ser Thr Ser Val Gly Asp Arg Val Ser Ile Thr Cys Lys
        35                  40                  45

Ala Ser Gln Asp Val Arg Thr Ala Val Ala Trp Tyr Gln Gln Lys Pro
    50                  55                  60

Gly Gln Ser Pro Lys Leu Leu Ile Tyr Trp Ala Ser Thr Arg His Thr
65                  70                  75                  80

Gly Val Pro Asp Arg Phe Thr Gly Ser Gly Ser Gly Thr Asp Tyr Thr
                85                  90                  95

Leu Thr Ile Ser Ser Val Gln Ala Glu Asp Leu Ala Leu Tyr Tyr Cys
            100                 105                 110

Gln Gln His Tyr Asn Thr Pro Pro Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235

<210> SEQ ID NO 11
<211> LENGTH: 5
<212> TYPE: PRT
<213> ORGANISM: Artificial
<220> FEATURE:
<223> OTHER INFORMATION: Amino acid sequence of heavy chain CDR1 of
      J15A7 antibody.

<400> SEQUENCE: 11

Asp Tyr Trp Met His
1               5

<210> SEQ ID NO 12
<211> LENGTH: 17
<212> TYPE: PRT
<213> ORGANISM: Artificial
<220> FEATURE:
<223> OTHER INFORMATION: Amino acid sequence of heavy chain CDR2 of
      J15A7 antibody.

<400> SEQUENCE: 12

Val Ile Asp Thr Ser Asp Ser Tyr Thr Ser Tyr Asn Gln Lys Phe Asn
1               5                   10                  15
Arg

<210> SEQ ID NO 13
<211> LENGTH: 7
<212> TYPE: PRT
<213> ORGANISM: Artificial
<220> FEATURE:
<223> OTHER INFORMATION: Amino acid sequence of heavy chain CDR3 of
      J15A7 antibody.

<400> SEQUENCE: 13

Asp Gly Pro Tyr Tyr Ala Met
1               5

<210> SEQ ID NO 14
<211> LENGTH: 10
<212> TYPE: PRT
<213> ORGANISM: Artificial
<220> FEATURE:
<223> OTHER INFORMATION: Amino acid sequence of light chain CDR1 of
      J15A7 antibody.

<400> SEQUENCE: 14

Ser Ala Ser Ser Gly Val Ser Tyr Met Tyr
1               5                   10

<210> SEQ ID NO 15
<211> LENGTH: 7
<212> TYPE: PRT
<213> ORGANISM: Artificial
<220> FEATURE:
<223> OTHER INFORMATION: Amino acid sequence of light chain CDR2 of
      J15A7 antibody.

<400> SEQUENCE: 15

Arg Thr Ser Asn Leu Ala Ser
1               5

<210> SEQ ID NO 16
<211> LENGTH: 6
<212> TYPE: PRT
<213> ORGANISM: Artificial
<220> FEATURE:
<223> OTHER INFORMATION: Amino acid sequence of light chain CDR3 of
      J15A7 antibody.

<400> SEQUENCE: 16

His Gln Tyr His Ser Asp
1               5

<210> SEQ ID NO 17
<211> LENGTH: 5
<212> TYPE: PRT
<213> ORGANISM: Artificial
<220> FEATURE:
<223> OTHER INFORMATION: Amino acid sequence of heavy chain CDR1 of
      B33A4 antibody.

<400> SEQUENCE: 17

Asp Tyr Asn Leu Asp
1               5

```
<210> SEQ ID NO 18
<211> LENGTH: 17
<212> TYPE: PRT
<213> ORGANISM: Artificial
<220> FEATURE:
<223> OTHER INFORMATION: Amino acid sequence of heavy chain CDR2 of
      B33A4 antibody.

<400> SEQUENCE: 18

Asp Ile Asn Pro Asn Thr Gly Gly Thr Ile Tyr Asn Gln Asn Phe Lys
1               5                   10                  15

Gly

<210> SEQ ID NO 19
<211> LENGTH: 7
<212> TYPE: PRT
<213> ORGANISM: Artificial
<220> FEATURE:
<223> OTHER INFORMATION: Amino acid sequence of heavy chain CDR3 of
      B33A4 antibody.

<400> SEQUENCE: 19

Tyr Phe Val Ser Asn Tyr Gly
1               5

<210> SEQ ID NO 20
<211> LENGTH: 11
<212> TYPE: PRT
<213> ORGANISM: Artificial
<220> FEATURE:
<223> OTHER INFORMATION: Amino acid sequence of light chain CDR1 of
      B33A4 antibody.

<400> SEQUENCE: 20

Lys Ala Ser Gln Ser Val Ser Tyr Asp Val Ala
1               5                   10

<210> SEQ ID NO 21
<211> LENGTH: 7
<212> TYPE: PRT
<213> ORGANISM: Artificial
<220> FEATURE:
<223> OTHER INFORMATION: Amino acid sequence of light chain CDR2 of
      B33A4 antibody.

<400> SEQUENCE: 21

Tyr Ala Ser Asn Leu Tyr Thr
1               5

<210> SEQ ID NO 22
<211> LENGTH: 6
<212> TYPE: PRT
<213> ORGANISM: Artificial
<220> FEATURE:
<223> OTHER INFORMATION: Amino acid sequence of light chain CDR3 of
      B33A4 antibody.

<400> SEQUENCE: 22

Gln Gln Asp Ser Ser Ser
1               5

<210> SEQ ID NO 23
<211> LENGTH: 5
<212> TYPE: PRT
<213> ORGANISM: Artificial
<220> FEATURE:
<223> OTHER INFORMATION: Amino acid sequence of heavy chain CDR1 of
      C34A1 antibody.
```

```
<400> SEQUENCE: 23

Ser Tyr Ala Met Ser
1               5

<210> SEQ ID NO 24
<211> LENGTH: 17
<212> TYPE: PRT
<213> ORGANISM: Artificial
<220> FEATURE:
<223> OTHER INFORMATION: Amino acid sequence of heavy chain CDR2 of
      C34A1 antibody.

<400> SEQUENCE: 24

Thr Ser Ser Ser Val Gly Ser Tyr Ala Tyr Tyr Pro Asp Asn Val Lys
1               5                   10                  15

Gly

<210> SEQ ID NO 25
<211> LENGTH: 10
<212> TYPE: PRT
<213> ORGANISM: Artificial
<220> FEATURE:
<223> OTHER INFORMATION: Amino acid sequence of heavy chain CDR3 of
      C34A1 antibody.

<400> SEQUENCE: 25

Ala Arg Arg Asp Tyr Asp Ala Arg Tyr Trp
1               5                   10

<210> SEQ ID NO 26
<211> LENGTH: 11
<212> TYPE: PRT
<213> ORGANISM: Artificial
<220> FEATURE:
<223> OTHER INFORMATION: Amino acid sequence of light chain CDR1 of
      C34A1 antibody.

<400> SEQUENCE: 26

Lys Ala Ser Gln Asp Ile Lys Ser Tyr Leu Ser
1               5                   10

<210> SEQ ID NO 27
<211> LENGTH: 7
<212> TYPE: PRT
<213> ORGANISM: Artificial
<220> FEATURE:
<223> OTHER INFORMATION: Amino acid sequence of light chain CDR2 of
      C34A1 antibody.

<400> SEQUENCE: 27

Tyr Ala Thr Thr Leu Ala Asp
1               5

<210> SEQ ID NO 28
<211> LENGTH: 5
<212> TYPE: PRT
<213> ORGANISM: Artificial
<220> FEATURE:
<223> OTHER INFORMATION: Amino acid sequence of light chain CDR3 of
      C34A1 antibody.

<400> SEQUENCE: 28

Leu Gln His Gly Glu
1               5
```

<210> SEQ ID NO 29
<211> LENGTH: 461
<212> TYPE: PRT
<213> ORGANISM: Artificial
<220> FEATURE:
<223> OTHER INFORMATION: Amino acid sequence of heavy chain of J15A7 antibody.

<400> SEQUENCE: 29

```
Met Arg Trp Ser Cys Ile Ser Leu Phe Leu Val Ala Thr Ala Thr Gly
1               5                   10                  15

Val Asn Ser Gln Val Gln Leu Gln Gln Pro Gly Ala Glu Leu Val Met
            20                  25                  30

Pro Gly Ala Ser Val Lys Met Ser Cys Lys Ala Ser Gly Tyr Thr Phe
        35                  40                  45

Thr Asp Tyr Trp Met His Trp Val Lys Gln Arg Pro Gly Gln Gly Leu
    50                  55                  60

Glu Trp Ile Gly Val Ile Asp Thr Ser Asp Ser Tyr Thr Ser Tyr Asn
65                  70                  75                  80

Gln Lys Phe Asn Arg Lys Ala Thr Leu Thr Val Asp Glu Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Asp Gly Pro Tyr Tyr Ala Met Asp Tyr Trp Gly
        115                 120                 125

Gln Gly Thr Ser Val Thr Val Ser Ser Ala Lys Thr Thr Pro Pro Ser
    130                 135                 140

Val Tyr Pro Leu Ala Pro Gly Ser Ala Ala Gln Thr Asn Ser Met Val
145                 150                 155                 160

Thr Leu Gly Cys Leu Val Lys Gly Tyr Phe Pro Glu Pro Val Thr Val
                165                 170                 175

Thr Trp Asn Ser Gly Ser Leu Ser Ser Gly Val His Thr Phe Pro Ala
            180                 185                 190

Val Leu Gln Ser Asp Leu Tyr Thr Leu Ser Ser Ser Val Thr Val Pro
        195                 200                 205

Ser Ser Thr Trp Pro Ser Glu Thr Val Thr Cys Asn Val Ala His Pro
    210                 215                 220

Ala Ser Ser Thr Lys Val Asp Lys Lys Ile Val Pro Arg Asp Cys Gly
225                 230                 235                 240

Cys Lys Pro Cys Ile Cys Thr Val Pro Glu Val Ser Ser Val Phe Ile
                245                 250                 255

Phe Pro Pro Lys Pro Lys Asp Val Leu Thr Ile Thr Leu Thr Pro Lys
            260                 265                 270

Val Thr Cys Val Val Val Asp Ile Ser Lys Asp Asp Pro Glu Val Gln
        275                 280                 285

Phe Ser Trp Phe Val Asp Asp Val Glu Val His Thr Ala Gln Thr Gln
    290                 295                 300

Pro Arg Glu Glu Gln Phe Asn Ser Thr Phe Arg Ser Val Ser Glu Leu
305                 310                 315                 320

Pro Ile Met His Gln Asp Trp Leu Asn Gly Lys Glu Phe Lys Cys Arg
                325                 330                 335

Val Asn Ser Ala Ala Phe Pro Ala Pro Ile Glu Lys Thr Ile Ser Lys
            340                 345                 350

Thr Lys Gly Arg Pro Lys Ala Pro Gln Val Tyr Thr Ile Pro Pro Pro
        355                 360                 365
```

```
Lys Glu Gln Met Ala Lys Asp Lys Val Ser Leu Thr Cys Met Ile Thr
        370                 375                 380

Asp Phe Pro Glu Asp Ile Thr Val Glu Trp Gln Trp Asn Gly Gln
385                 390                 395                 400

Pro Ala Glu Asn Tyr Lys Asn Thr Gln Pro Ile Met Asp Thr Asp Gly
                405                 410                 415

Ser Tyr Phe Val Tyr Ser Lys Leu Asn Val Gln Lys Ser Asn Trp Glu
                420                 425                 430

Ala Gly Asn Thr Phe Thr Cys Ser Val Leu His Glu Gly Leu His Asn
                435                 440                 445

His His Thr Glu Lys Ser Leu Ser His Ser Pro Gly Lys
        450                 455                 460

<210> SEQ ID NO 30
<211> LENGTH: 235
<212> TYPE: PRT
<213> ORGANISM: Artificial
<220> FEATURE:
<223> OTHER INFORMATION: Amino acid sequence of light chain of J15A7
      antibody.

<400> SEQUENCE: 30

Met Asp Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Pro Gly Glu Lys Val Thr Ile Ser Cys Ser Ala Ser
        35                  40                  45

Ser Gly Val Ser Tyr Met Tyr Trp Tyr Gln Gln Lys Pro Gly Ser Ser
    50                  55                  60

Pro Lys Pro Trp Ile Tyr Arg Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys His Gln Tyr
            100                 105                 110

His Ser Asp Pro Arg Thr Phe Gly Gly Gly Thr Lys Leu Glu Ile Lys
        115                 120                 125

Arg Ala Asp Ala Ala Pro Thr Val Ser Ile Phe Pro Pro Ser Ser Glu
    130                 135                 140

Gln Leu Thr Ser Gly Gly Ala Ser Val Val Cys Phe Leu Asn Asn Phe
145                 150                 155                 160

Tyr Pro Lys Asp Ile Asn Val Lys Trp Lys Ile Asp Gly Ser Glu Arg
                165                 170                 175

Gln Asn Gly Val Leu Asn Ser Trp Thr Asp Gln Asp Ser Lys Asp Ser
            180                 185                 190

Thr Tyr Ser Met Ser Ser Thr Leu Thr Leu Thr Lys Asp Glu Tyr Glu
        195                 200                 205

Arg His Asn Ser Tyr Thr Cys Glu Ala Thr His Lys Thr Ser Thr Ser
    210                 215                 220

Pro Ile Val Lys Ser Phe Asn Arg Asn Glu Cys
225                 230                 235

<210> SEQ ID NO 31
<211> LENGTH: 482
<212> TYPE: PRT
<213> ORGANISM: Artificial
```

<220> FEATURE:
<223> OTHER INFORMATION: Amino acid sequence of heavy chain of B33A4 antibody.

<400> SEQUENCE: 31

```
Met Ser Ser Pro Gln Ala Leu Asn Thr Leu Thr Leu Thr Met Gly Trp
1               5                   10                  15

Ser Trp Ile Phe Leu Phe Phe Leu Ser Gly Thr Ala Gly Val Leu Ser
            20                  25                  30

Glu Val Leu Leu Gln Gln Ser Gly Pro Glu Leu Val Lys Pro Gly Ala
        35                  40                  45

Ser Val Lys Ile Pro Cys Lys Ala Ser Gly Phe Thr Phe Thr Asp Tyr
    50                  55                  60

Asn Leu Asp Trp Val Lys Gln Ser His Glu Lys Ser Leu Glu Trp Ile
65                  70                  75                  80

Gly Asp Ile Asn Pro Asn Thr Gly Gly Thr Ile Tyr Asn Gln Asn Phe
                85                  90                  95

Lys Gly Lys Ala Thr Leu Thr Val Asp Arg Ser Ser Gly Thr Ala Tyr
            100                 105                 110

Met Glu Leu Arg Ser Leu Thr Ser Glu Asp Thr Ala Val Tyr Phe Cys
        115                 120                 125

Ala Arg Tyr Phe Val Ser Asn Tyr Gly Tyr Phe Asp Val Trp Gly Ala
    130                 135                 140

Gly Thr Thr Val Thr Val Ser Ser Ala Lys Thr Thr Ala Pro Ser Val
145                 150                 155                 160

Tyr Pro Leu Ala Pro Val Cys Gly Asp Thr Thr Gly Ser Ser Val Thr
                165                 170                 175

Leu Gly Cys Leu Val Lys Gly Tyr Phe Pro Glu Pro Val Thr Leu Thr
            180                 185                 190

Trp Asn Ser Gly Ser Leu Ser Ser Gly Val His Thr Phe Pro Ala Val
        195                 200                 205

Leu Gln Ser Asp Leu Tyr Thr Leu Ser Ser Ser Val Thr Val Thr Ser
    210                 215                 220

Ser Thr Trp Pro Ser Gln Ser Ile Thr Cys Asn Val Ala His Pro Ala
225                 230                 235                 240

Ser Ser Thr Lys Val Asp Lys Lys Ile Glu Pro Arg Gly Pro Thr Ile
                245                 250                 255

Lys Pro Cys Pro Pro Cys Lys Cys Pro Ala Pro Asn Leu Leu Gly Gly
            260                 265                 270

Pro Ser Val Phe Ile Phe Pro Pro Lys Ile Lys Asp Val Leu Met Ile
        275                 280                 285

Ser Leu Ser Pro Ile Val Thr Cys Val Val Val Asp Val Ser Glu Asp
    290                 295                 300

Asp Pro Asp Val Gln Ile Ser Trp Phe Val Asn Asn Val Glu Val His
305                 310                 315                 320

Thr Ala Gln Thr Gln Thr His Arg Glu Asp Tyr Asn Ser Thr Leu Arg
                325                 330                 335

Val Val Ser Ala Leu Pro Ile Gln His Gln Asp Trp Met Ser Gly Lys
            340                 345                 350

Glu Phe Lys Cys Lys Val Asn Asn Lys Asp Leu Pro Ala Pro Ile Glu
        355                 360                 365

Arg Thr Ile Ser Lys Pro Lys Gly Ser Val Arg Ala Pro Gln Val Tyr
    370                 375                 380

Val Leu Pro Pro Pro Glu Glu Glu Met Thr Lys Lys Gln Val Thr Leu
```

```
                385                 390                 395                 400
        Thr Cys Met Val Thr Asp Phe Met Pro Glu Asp Ile Tyr Val Glu Trp
                        405                 410                 415
        Thr Asn Asn Gly Lys Thr Glu Leu Asn Tyr Lys Asn Thr Glu Pro Val
                        420                 425                 430
        Leu Asp Ser Asp Gly Ser Tyr Phe Met Tyr Ser Lys Leu Arg Val Glu
                        435                 440                 445
        Lys Lys Asn Trp Val Glu Arg Asn Ser Tyr Ser Cys Ser Val Val His
                        450                 455                 460
        Glu Gly Leu His Asn His His Thr Thr Lys Ser Phe Ser Arg Thr Pro
        465                 470                 475                 480
        Gly Lys

<210> SEQ ID NO 32
<211> LENGTH: 234
<212> TYPE: PRT
<213> ORGANISM: Artificial
<220> FEATURE:
<223> OTHER INFORMATION: Amino acid sequence of light chain of B33A4
      antibody.

<400> SEQUENCE: 32

Met Lys Ser Gln Thr Gln Val Phe Val Phe Leu Leu Leu Cys Val Ser
1               5                   10                  15

Gly Ala His Gly Ser Ile Val Met Thr Gln Thr Pro Lys Phe Leu Leu
                20                  25                  30

Val Ser Ala Gly Asp Arg Val Thr Ile Thr Cys Lys Ala Ser Gln Ser
            35                  40                  45

Val Ser Tyr Asp Val Ala Trp Tyr Gln Gln Lys Pro Gly Gln Ser Pro
        50                  55                  60

Lys Leu Leu Ile Tyr Tyr Ala Ser Asn Leu Tyr Thr Gly Val Pro Asp
65                  70                  75                  80

Arg Phe Thr Gly Ser Gly Tyr Gly Thr Asp Phe Thr Phe Thr Ile Ser
                85                  90                  95

Thr Val Gln Ala Glu Asp Leu Ala Val Tyr Phe Cys Gln Gln Asp Ser
                100                 105                 110

Ser Ser Pro Tyr Thr Phe Gly Gly Gly Thr Lys Leu Glu Ile Lys Arg
            115                 120                 125

Ala Asp Ala Ala Pro Thr Val Ser Ile Phe Pro Pro Ser Ser Glu Gln
        130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
                180                 185                 190

Tyr Ser Met Ser Ser Thr Leu Thr Leu Thr Lys Asp Glu Tyr Glu Arg
            195                 200                 205

His Asn Ser Tyr Thr Cys Glu Ala Thr His Lys Thr Ser Thr Ser Pro
        210                 215                 220

Ile Val Lys Ser Phe Asn Arg Asn Glu Cys
225                 230

<210> SEQ ID NO 33
<211> LENGTH: 470
<212> TYPE: PRT
```

<213> ORGANISM: Artificial
<220> FEATURE:
<223> OTHER INFORMATION: Amino acid sequence of heavy chain of C34A1 antibody.

<400> SEQUENCE: 33

Met Asn Phe Gly Leu Ser Leu Ile Phe Leu Ala Leu Ile Leu Lys Gly
1               5                   10                  15

Val Gln Cys Glu Val Gln Leu Val Glu Ser Gly Gly Asp Leu Val Lys
            20                  25                  30

Pro Gly Gly Ser Leu Lys Leu Ser Cys Ala Ala Ser Gly Phe Thr Phe
        35                  40                  45

Ser Ser Tyr Ala Met Ser Trp Val Arg Gln Thr Pro Asp Asn Arg Leu
50                  55                  60

Glu Trp Val Ala Thr Ser Ser Val Gly Ser Tyr Ala Tyr Tyr Pro
65                  70                  75                  80

Asp Asn Val Lys Gly Arg Phe Thr Ile Ser Arg Asp Asn Ala Lys Asn
                85                  90                  95

Thr Leu Tyr Leu Gln Met Ser Ser Leu Lys Ser Glu Asp Thr Ala Met
            100                 105                 110

Tyr Tyr Cys Ala Arg Arg Asp Tyr Asp Ala Arg Tyr Trp Tyr Phe Asp
        115                 120                 125

Val Trp Gly Ala Gly Thr Thr Val Thr Val Ser Ser Ala Lys Thr Thr
130                 135                 140

Ala Pro Ser Val Tyr Pro Leu Ala Pro Val Cys Gly Asp Thr Thr Gly
145                 150                 155                 160

Ser Ser Val Thr Leu Gly Cys Leu Val Lys Gly Tyr Phe Pro Glu Pro
                165                 170                 175

Val Thr Leu Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Thr Ser Ser Thr Trp Pro Ser Gln Ser Ile Thr Cys Asn Val
210                 215                 220

Ala His Pro Ala Ser Ser Thr Lys Val Asp Lys Lys Ile Glu Pro Arg
225                 230                 235                 240

Gly Pro Thr Ile Lys Pro Cys Pro Pro Cys Lys Cys Pro Ala Pro Asn
                245                 250                 255

Leu Leu Gly Gly Pro Ser Val Phe Ile Phe Pro Pro Lys Ile Lys Asp
            260                 265                 270

Val Leu Met Ile Ser Leu Ser Pro Ile Val Thr Cys Val Val Val Asp
        275                 280                 285

Val Ser Glu Asp Asp Pro Asp Val Gln Ile Ser Trp Phe Val Asn Asn
290                 295                 300

Val Glu Val His Thr Ala Gln Thr Gln Thr His Arg Glu Asp Tyr Asn
305                 310                 315                 320

Ser Thr Leu Arg Val Val Ser Ala Leu Pro Ile Gln His Gln Asp Trp
                325                 330                 335

Met Ser Gly Lys Glu Phe Lys Cys Lys Val Asn Asn Lys Asp Leu Pro
            340                 345                 350

Ala Pro Ile Glu Arg Thr Ile Ser Lys Pro Lys Gly Ser Val Arg Ala
        355                 360                 365

Pro Gln Val Tyr Val Leu Pro Pro Glu Glu Glu Met Thr Lys Lys
370                 375                 380

```
Gln Val Thr Leu Thr Cys Met Val Thr Asp Phe Met Pro Glu Asp Ile
385                 390                 395                 400

Tyr Val Glu Trp Thr Asn Asn Gly Lys Thr Glu Leu Asn Tyr Lys Asn
                405                 410                 415

Thr Glu Pro Val Leu Asp Ser Asp Gly Ser Tyr Phe Met Tyr Ser Lys
            420                 425                 430

Leu Arg Val Glu Lys Lys Asn Trp Val Glu Arg Asn Ser Tyr Ser Cys
        435                 440                 445

Ser Val Val His Glu Gly Leu His Asn His His Thr Thr Lys Ser Phe
    450                 455                 460

Ser Arg Thr Pro Gly Lys
465             470

<210> SEQ ID NO 34
<211> LENGTH: 236
<212> TYPE: PRT
<213> ORGANISM: Artificial
<220> FEATURE:
<223> OTHER INFORMATION: Amino acid sequence of light chain of C34A1
      antibody.

<400> SEQUENCE: 34

Met Asp Met Arg Ala Pro Ala Gln Phe Phe Gly Ile Leu Leu Leu Trp
1               5                   10                  15

Phe Pro Gly Ile Arg Cys Asp Ile Lys Met Thr Gln Ser Pro Ser Ser
            20                  25                  30

Met Tyr Ala Ser Leu Gly Glu Arg Val Thr Ile Thr Cys Lys Ala Ser
        35                  40                  45

Gln Asp Ile Lys Ser Tyr Leu Ser Trp Tyr Gln Leu Lys Pro Trp Lys
    50                  55                  60

Ser Pro Lys Thr Leu Ile Tyr Tyr Ala Thr Thr Leu Ala Asp Gly Val
65                  70                  75                  80

Pro Ser Arg Phe Ser Gly Ser Gly Ser Gly Gln Asp Tyr Ser Leu Thr
                85                  90                  95

Ile Ser Ser Leu Glu Ser Asp Asp Thr Ala Thr Tyr Tyr Cys Leu Gln
            100                 105                 110

His Gly Glu Ser Pro Tyr Thr Phe Gly Gly Gly Thr Lys Leu Glu Ile
        115                 120                 125

Lys Arg Ala Asp Ala Ala Pro Thr Val Ser Ile Phe Pro Pro Ser Ser
    130                 135                 140

Glu Gln Leu Thr Ser Gly Gly Ala Ser Val Val Cys Phe Leu Asn Asn
145                 150                 155                 160

Phe Tyr Pro Lys Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
            180                 185                 190

Ser Thr Tyr Ser Met Ser Ser Thr Leu Thr Leu Thr Lys Asp Glu Tyr
        195                 200                 205

Glu Arg His Asn Ser Tyr Thr Cys Glu Ala Thr His Lys Thr Ser Thr
    210                 215                 220

Ser Pro Ile Val Lys Ser Phe Asn Arg Asn Glu Cys
225                 230                 235

<210> SEQ ID NO 35
<211> LENGTH: 20
<212> TYPE: DNA
<213> ORGANISM: Mus musculus
```

```
<220> FEATURE:
<221> NAME/KEY: misc_feature
<223> OTHER INFORMATION: DNA sequence of CpGB.

<400> SEQUENCE: 35
tccatgacgt tcctgatgct                                                   20

<210> SEQ ID NO 36
<211> LENGTH: 20
<212> TYPE: DNA
<213> ORGANISM: Mus musculus
<220> FEATURE:
<221> NAME/KEY: misc_feature
<223> OTHER INFORMATION: DNA sequence of CpGA.

<400> SEQUENCE: 36
ggggtcaacg ttgagggggg                                                   20

<210> SEQ ID NO 37
<211> LENGTH: 19
<212> TYPE: RNA
<213> ORGANISM: Artificial
<220> FEATURE:
<223> OTHER INFORMATION: RNA sequence of PolyU.

<400> SEQUENCE: 37
uuuuuuuuuu uuuuuuuuu                                                    19

<210> SEQ ID NO 38
<211> LENGTH: 20
<212> TYPE: RNA
<213> ORGANISM: Mus musculus
<220> FEATURE:
<221> NAME/KEY: misc_feature
<223> OTHER INFORMATION: RNA sequence of RNA9.2s-DR.

<400> SEQUENCE: 38
uguccuucaa uguccuucaa                                                   20

<210> SEQ ID NO 39
<211> LENGTH: 1049
<212> TYPE: PRT
<213> ORGANISM: Homo sapiens
<220> FEATURE:
<221> NAME/KEY: MISC_FEATURE
<223> OTHER INFORMATION: Amino acid sequence of human TLR7.

<400> SEQUENCE: 39

Met Val Phe Pro Met Trp Thr Leu Lys Arg Gln Ile Leu Ile Leu Phe
1               5                   10                  15

Asn Ile Ile Leu Ile Ser Lys Leu Leu Gly Ala Arg Trp Phe Pro Lys
            20                  25                  30

Thr Leu Pro Cys Asp Val Thr Leu Asp Val Pro Lys Asn His Val Ile
        35                  40                  45

Val Asp Cys Thr Asp Lys His Leu Thr Glu Ile Pro Gly Gly Ile Pro
    50                  55                  60

Thr Asn Thr Thr Asn Leu Thr Leu Thr Ile Asn His Ile Pro Asp Ile
65                  70                  75                  80

Ser Pro Ala Ser Phe His Arg Leu Asp His Leu Val Glu Ile Asp Phe
                85                  90                  95

Arg Cys Asn Cys Val Pro Ile Pro Leu Gly Ser Lys Asn Asn Met Cys
            100                 105                 110

Ile Lys Arg Leu Gln Ile Lys Pro Arg Ser Phe Ser Gly Leu Thr Tyr
```

```
            115                 120                 125
Leu Lys Ser Leu Tyr Leu Asp Gly Asn Gln Leu Leu Glu Ile Pro Gln
130                 135                 140
Gly Leu Pro Pro Ser Leu Gln Leu Leu Ser Leu Glu Ala Asn Asn Ile
145                 150                 155                 160
Phe Ser Ile Arg Lys Glu Asn Leu Thr Glu Leu Ala Asn Ile Glu Ile
                165                 170                 175
Leu Tyr Leu Gly Gln Asn Cys Tyr Tyr Arg Asn Pro Cys Tyr Val Ser
                180                 185                 190
Tyr Ser Ile Glu Lys Asp Ala Phe Leu Asn Leu Thr Lys Leu Lys Val
            195                 200                 205
Leu Ser Leu Lys Asp Asn Asn Val Thr Ala Val Pro Thr Val Leu Pro
210                 215                 220
Ser Thr Leu Thr Glu Leu Tyr Leu Tyr Asn Asn Met Ile Ala Lys Ile
225                 230                 235                 240
Gln Glu Asp Asp Phe Asn Asn Leu Asn Gln Leu Gln Ile Leu Asp Leu
                245                 250                 255
Ser Gly Asn Cys Pro Arg Cys Tyr Asn Ala Pro Phe Pro Cys Ala Pro
                260                 265                 270
Cys Lys Asn Asn Ser Pro Leu Gln Ile Pro Val Asn Ala Phe Asp Ala
            275                 280                 285
Leu Thr Glu Leu Lys Val Leu Arg Leu His Ser Asn Ser Leu Gln His
290                 295                 300
Val Pro Pro Arg Trp Phe Lys Asn Ile Asn Lys Leu Gln Glu Leu Asp
305                 310                 315                 320
Leu Ser Gln Asn Phe Leu Ala Lys Glu Ile Gly Asp Ala Lys Phe Leu
                325                 330                 335
His Phe Leu Pro Ser Leu Ile Gln Leu Asp Leu Ser Phe Asn Phe Glu
                340                 345                 350
Leu Gln Val Tyr Arg Ala Ser Met Asn Leu Ser Gln Ala Phe Ser Ser
            355                 360                 365
Leu Lys Ser Leu Lys Ile Leu Arg Ile Arg Gly Tyr Val Phe Lys Glu
370                 375                 380
Leu Lys Ser Phe Asn Leu Ser Pro Leu His Asn Leu Gln Asn Leu Glu
385                 390                 395                 400
Val Leu Asp Leu Gly Thr Asn Phe Ile Lys Ile Ala Asn Leu Ser Met
                405                 410                 415
Phe Lys Gln Phe Lys Arg Leu Lys Val Ile Asp Leu Ser Val Asn Lys
                420                 425                 430
Ile Ser Pro Ser Gly Asp Ser Ser Glu Val Gly Phe Cys Ser Asn Ala
            435                 440                 445
Arg Thr Ser Val Glu Ser Tyr Glu Pro Gln Val Leu Glu Gln Leu His
450                 455                 460
Tyr Phe Arg Tyr Asp Lys Tyr Ala Arg Ser Cys Arg Phe Lys Asn Lys
465                 470                 475                 480
Glu Ala Ser Phe Met Ser Val Asn Glu Ser Cys Tyr Lys Tyr Gly Gln
                485                 490                 495
Thr Leu Asp Leu Ser Lys Asn Ser Ile Phe Phe Val Lys Ser Ser Asp
                500                 505                 510
Phe Gln His Leu Ser Phe Leu Lys Cys Leu Asn Leu Ser Gly Asn Leu
            515                 520                 525
Ile Ser Gln Thr Leu Asn Gly Ser Glu Phe Gln Pro Leu Ala Glu Leu
530                 535                 540
```

```
Arg Tyr Leu Asp Phe Ser Asn Asn Arg Leu Asp Leu His Ser Thr
545                 550                 555                 560

Ala Phe Glu Glu Leu His Lys Leu Glu Val Leu Asp Ile Ser Ser Asn
                565                 570                 575

Ser His Tyr Phe Gln Ser Glu Gly Ile Thr His Met Leu Asn Phe Thr
            580                 585                 590

Lys Asn Leu Lys Val Leu Gln Lys Leu Met Met Asn Asp Asn Asp Ile
        595                 600                 605

Ser Ser Ser Thr Ser Arg Thr Met Glu Ser Glu Ser Leu Arg Thr Leu
610                 615                 620

Glu Phe Arg Gly Asn His Leu Asp Val Leu Trp Arg Glu Gly Asp Asn
625                 630                 635                 640

Arg Tyr Leu Gln Leu Phe Lys Asn Leu Leu Lys Leu Glu Glu Leu Asp
                645                 650                 655

Ile Ser Lys Asn Ser Leu Ser Phe Leu Pro Ser Gly Val Phe Asp Gly
            660                 665                 670

Met Pro Pro Asn Leu Lys Asn Leu Ser Leu Ala Lys Asn Gly Leu Lys
        675                 680                 685

Ser Phe Ser Trp Lys Lys Leu Gln Cys Leu Lys Asn Leu Glu Thr Leu
690                 695                 700

Asp Leu Ser His Asn Gln Leu Thr Thr Val Pro Glu Arg Leu Ser Asn
705                 710                 715                 720

Cys Ser Arg Ser Leu Lys Asn Leu Ile Leu Lys Asn Asn Gln Ile Arg
                725                 730                 735

Ser Leu Thr Lys Tyr Phe Leu Gln Asp Ala Phe Gln Leu Arg Tyr Leu
            740                 745                 750

Asp Leu Ser Ser Asn Lys Ile Gln Met Ile Gln Lys Thr Ser Phe Pro
        755                 760                 765

Glu Asn Val Leu Asn Asn Leu Lys Met Leu Leu Leu His His Asn Arg
770                 775                 780

Phe Leu Cys Thr Cys Asp Ala Val Trp Phe Val Trp Trp Val Asn His
785                 790                 795                 800

Thr Glu Val Thr Ile Pro Tyr Leu Ala Thr Asp Val Thr Cys Val Gly
                805                 810                 815

Pro Gly Ala His Lys Gly Gln Ser Val Ile Ser Leu Asp Leu Tyr Thr
            820                 825                 830

Cys Glu Leu Asp Leu Thr Asn Leu Ile Leu Phe Ser Leu Ser Ile Ser
        835                 840                 845

Val Ser Leu Phe Leu Met Val Met Met Thr Ala Ser His Leu Tyr Phe
850                 855                 860

Trp Asp Val Trp Tyr Ile Tyr His Phe Cys Lys Ala Lys Ile Lys Gly
865                 870                 875                 880

Tyr Gln Arg Leu Ile Ser Pro Asp Cys Cys Tyr Asp Ala Phe Ile Val
                885                 890                 895

Tyr Asp Thr Lys Asp Pro Ala Val Thr Glu Trp Val Leu Ala Glu Leu
            900                 905                 910

Val Ala Lys Leu Glu Asp Pro Arg Glu Lys His Phe Asn Leu Cys Leu
        915                 920                 925

Glu Glu Arg Asp Trp Leu Pro Gly Gln Pro Val Leu Glu Asn Leu Ser
930                 935                 940

Gln Ser Ile Gln Leu Ser Lys Lys Thr Val Phe Val Met Thr Asp Lys
945                 950                 955                 960
```

```
Tyr Ala Lys Thr Glu Asn Phe Lys Ile Ala Phe Tyr Leu Ser His Gln
                965                 970                 975

Arg Leu Met Asp Glu Lys Val Asp Val Ile Ile Leu Ile Phe Leu Glu
            980                 985                 990

Lys Pro Phe Gln Lys Ser Lys Phe Leu Gln Leu Arg Lys Arg Leu Cys
        995                1000                1005

Gly Ser Ser Val Leu Glu Trp Pro Thr Asn Pro Gln Ala His Pro
    1010                1015                1020

Tyr Phe Trp Gln Cys Leu Lys Asn Ala Leu Ala Thr Asp Asn His
    1025                1030                1035

Val Ala Tyr Ser Gln Val Phe Lys Glu Thr Val
    1040                1045

<210> SEQ ID NO 40
<211> LENGTH: 20
<212> TYPE: PRT
<213> ORGANISM: Mus musculus

<400> SEQUENCE: 40

Ala Asp Pro His Pro Ala Pro Leu Ser Thr Pro Ala Ser Lys Asn Phe
1               5                   10                  15

Met Asp Arg Cys
            20

<210> SEQ ID NO 41
<211> LENGTH: 20
<212> TYPE: PRT
<213> ORGANISM: Homo sapiens

<400> SEQUENCE: 41

Gly Asp Leu Ala Pro Ala Pro Val Asp Thr Pro Ser Ser Glu Asp Phe
1               5                   10                  15

Arg Pro Asn Cys
            20

<210> SEQ ID NO 42
<211> LENGTH: 20
<212> TYPE: PRT
<213> ORGANISM: Artificial Sequence
<220> FEATURE:
<223> OTHER INFORMATION: Synthetic

<400> SEQUENCE: 42

Ser Val Asp Arg His Gly Pro Gln Val Leu Glu Ala Leu His Tyr Phe
1               5                   10                  15

Arg Tyr Asp Glu
            20

<210> SEQ ID NO 43
<211> LENGTH: 10
<212> TYPE: PRT
<213> ORGANISM: Artificial Sequence
<220> FEATURE:
<223> OTHER INFORMATION: Synthetic

<400> SEQUENCE: 43

Pro Gln Val Leu Glu Ala Leu His Tyr Phe
1               5                   10
```

PREVENTIVE OR THERAPEUTIC AGENT FOR INFLAMMATORY DISEASE

TECHNICAL FIELD

The present invention relates to a preventive or therapeutic agent for inflammatory diseases containing an antibody against a Toll-like receptor (TLR) 7 or 9.

BACKGROUND ART

TLRs form a family of pathogen sensors. They respond to a pathogen component, induce an activation signal, and induce a phylactic response. TLRs are not only important for phylaxis but also involved in inflammation induction in disease conditions of autoimmune diseases and the like.

Of about 10 kinds of TLRs, TLR3, TLR7, TLR8, and TLR9 are distributed in endoplasmic reticula which are intracellular organelles and recognize bacteria- or virus-derived nucleic acids. TLR7 and TLR8 recognize single-stranded RNA, while TLR9 recognizes unmethylated single-stranded DNA (CpG-DNA) containing CpG motifs.

Since different from two-stranded RNA specific to virus, single-stranded RNA or DNA does not greatly differ from a nucleic acid derived from a host, TLRs cause a response against own cells, leading to an autoimmune disease, without precise control of their ligand recognition mechanism.

In this respect, the autoimmune response by TLR7 is controlled by limiting a nucleic acid recognition site to endo lysosomes (Non-patent Document 1). In a stationary state, extracellular self-nucleic acids are degraded rapidly so that they do not reach intracellular endo lysosomes and therefore, are not recognized by TLR7. On the other hand, microorganism nucleic acids protected by cell walls of bacteria or virions reach endo lysosomes and there, they are released for the first time and recognized by TLR7.

When self-nucleic acids acquire resistance against degradation due to mutual action with an anti-microorganism peptide or autoantibody and can reach endo lysosomes, TLR7-dependent autoimmune response is caused. In fact, relation of TLR7 to psoriasis or systemic lupus erythematosus (SLE) is suggested (Non-patent Documents 2 to 4).

TLR7 is therefore thought to be a therapeutic target in TLR7-dependent autoimmune diseases such as psoriasis and SLE and various methods for suppressing expression or function of TLR7 have hitherto been proposed. More specifically, a method of using an oligo DNA having an antagonism against TLR7 or a micro RNA for suppressing expression of TLR7 has been tried. In general, however, safety of nucleic acid drugs is unknown. In addition, it cannot be denied that the complete inhibition of the function of TLR7 may cause a risk such as infectious diseases.

From the standpoint of safety and specificity, antibody drugs are desired. As described above, however, TLR7 has been thought to be present only in endo lysosomes and isolated from the cell surface for limiting an immune response, which has prevented use of antibodies acting only on the cell surface. As a result, there has been no attempt to use an antibody drug.

It is reported that similar to TLR7, TLR9 is involved in the disease condition of psoriasis (Non-patent Document 2).

TLR9 also has been thought to be a therapeutic target of autoimmune diseases such as psoriasis and SLE. Similarly, expression of it in the cell surface has been thought not to occur. As a result, there has been no attempt to use an antibody drug.

CITATION LIST

Non-Patent Document(s)

Non-Patent Document 1: Barton, G. et al. d Medzhitov, R. Nat Immunol 7, 49-56. (2006).
Non-Patent Document 2: Lande, R. et al. Nature 449, 564-569 (2007).
Non-Patent Document 3: Christensen, S. R. et al. Immunity 25, 417-428 (2006).
Non-Patent Document 4: Ehlers, M. et al. J Exp Med 203, 553-561 (2006).

DISCLOSURE OF THE INVENTION

Problem to be Solved by the Invention

An object of the present invention is to provide a highly safe and highly specific preventive or therapeutic agent for inflammatory diseases targeting a TLR7 or TLR9 molecule.

Means for Solving the Problem

With a view to overcoming the above-described problem, the present inventors have proceeded with a research. As a result, it has been found that TLR7 and TLR9 are expressed also in the cell surface, contrary to traditional understanding that they are present locally in cells and isolated from the cell surface.

In addition, it has been confirmed that an anti-TLR7 antibody inhibits response to TLR7 in spleen-derived B cells, bone marrow-derived macrophages (BM-MCs), bone marrow-derived classical dendritic cells (BM-cDCs), and bone marrow-derived plasmacytoid dendritic cells (BM-pDCs). It has been confirmed further that based on the verification that administration of the anti-TLR7 antibody to an inflammatory disease mouse model significantly improves the disease condition, the anti-TLR7 antibody inhibits inflammatory cytokine produced by the in vivo administration of a TLR7 ligand, and the anti-TLR7 antibody also inhibits inflammation in psoriasis mouse model, cell surface TLR7 and TLR9, the existence of which has not hitherto been recognized, are useful as a target of an inflammatory disease, leading to completion of the present invention.

The present invention relates to:

[1] a therapeutic agent or preventive for an inflammatory disease containing an anti-TLR7 antibody or an anti-TLR9 antibody;

[2] the therapeutic agent or preventive for an inflammatory disease as described above in [1], wherein the anti-TLR7 antibody contains at least one of CDRs described below:

(a) a heavy chain CDR1 having an amino acid sequence represented by SEQ ID NO: 3;
(b) a heavy chain CDR2 having an amino acid sequence represented by SEQ ID NO: 4;
(c) a heavy chain CDR3 having an amino acid sequence represented by SEQ ID NO: 5;
(d) a light chain CDR1 having an amino acid sequence represented by SEQ ID NO: 6;
(e) a light chain CDR2 having an amino acid sequence represented by SEQ ID NO: 7;
(f) a light chain CDR3 having an amino acid sequence represented by SEQ ID NO: 8;

(g) a CDR having any of the amino acid sequences represented by SEQ ID NOs: 3 to 8 and having therein deletion, substitution, or addition of one or two amino acids; and (h) a CDR having an amino acid sequence having at least 90% homology with any of the amino acid sequences represented by SEQ ID NOs: from 3 to 8;

[3] the therapeutic agent or preventive for an inflammatory disease as described above in [1], wherein the TLR7 antibody is any of antibodies described below:

(1) an antibody containing a heavy chain having an amino acid sequence represented by SEQ ID NO: 9 and a light chain having an amino acid sequence represented by SEQ ID NO: 10;

(2) an antibody containing a heavy chain and/or a light chain having the amino acid sequence represented by SEQ ID NO: 9 and/or 10 and having therein deletion, substitution or addition of one or several amino acids; and (3) an antibody containing a heavy chain and/or light chain having an amino acid sequence having at least 70% homology with the amino acid sequence represented by SEQ ID NO: 9 and/or 10;

[4] the therapeutic agent or preventive for an inflammatory disease as described above in [1], wherein the anti-TLR7 antibody specifically binds to a region from position 27 to position 457 of an amino acid sequence of TLR7 represented by SEQ ID NO: 1;

[5] the therapeutic agent or preventive for an inflammatory disease as described above in [1], wherein the anti-TLR7 antibody specifically binds to a region from position 228 to position 364 of an amino acid sequence of mouse TLR7 represented by SEQ ID NO: 1 or an amino acid sequence of human TLR7 represented by SEQ ID NO: 39;

[6] the therapeutic agent or preventive for an inflammatory disease as described above in [1], wherein the anti-TLR7 antibody specifically binds to a region including a region from position 275 to position 313 of an amino acid sequence of mouse TLR7 represented by SEQ ID NO: 1 or an amino acid sequence of human TLR7 represented by SEQ ID NO: 39;

[7] the therapeutic agent or preventive for an inflammatory disease as described above in [1], wherein the anti-TLR7 antibody specifically binds to a region including a region from position 313 to position 364 of an amino acid sequence of mouse TLR7 represented by SEQ ID NO: 1 or an amino acid sequence of human TLR7 represented by SEQ ID NO: 39;

[8] the therapeutic agent or preventive for an inflammatory disease as described above in [1], wherein the anti-TLR9 antibody contains at least one of CDRs described below:

(a) a heavy chain CDR1 having an amino acid sequence represented by SEQ ID NO: 11;

(b) a heavy chain CDR2 having an amino acid sequence represented by SEQ ID NO: 12;

(c) a heavy chain CDR3 having an amino acid sequence represented by SEQ ID NO: 13;

(d) a light chain CDR1 having an amino acid sequence represented by SEQ ID NO: 14;

(e) a light chain CDR2 having an amino acid sequence represented by SEQ ID NO: 15;

(f) a light chain CDR3 having an amino acid sequence represented by SEQ ID NO: 16;

(g) a CDR having any of the amino acid sequences represented by SEQ ID NOs: 11 to 16 and having therein deletion, substitution, or addition of one or two amino acids; and (h) a CDR having an amino acid sequence having at least 90% homology with any of the amino acid sequences represented by SEQ ID NOs: 11 to 16;

[9] the therapeutic agent or preventive for an inflammatory disease as described above in [1], wherein the anti-TLR9 antibody contains at least one of CDRs described below:

(a) a heavy chain CDR1 having an amino acid sequence represented by SEQ ID NO: 17;

(b) a heavy chain CDR2 having an amino acid sequence represented by SEQ ID NO: 18;

(c) a heavy chain CDR3 having an amino acid sequence represented by SEQ ID NO: 19;

(d) a light chain CDR1 having an amino acid sequence represented by SEQ ID NO: 20;

(e) a light chain CDR2 having an amino acid sequence represented by SEQ ID NO: 21;

(f) a light chain CDR3 having an amino acid sequence represented by SEQ ID NO: 22;

(g) a CDR having any of the amino acid sequences represented by SEQ ID NOs: 17 to 22 and having therein deletion, substitution, or addition of one or two amino acids; and (h) a CDR having an amino acid sequence having at least 90% homology with any of the amino acid sequences represented by SEQ ID NOs: 17 to 22;

[10] the therapeutic agent or preventive for an inflammatory disease as described above in [1], wherein the anti-TLR9 antibody contains at least one of CDRs described below:

(a) a heavy chain CDR1 having an amino acid sequence represented by SEQ ID NO: 23;

(b) a heavy chain CDR2 having an amino acid sequence represented by SEQ ID NO: 24;

(c) a heavy chain CDR3 having an amino acid sequence represented by SEQ ID NO: 25;

(d) a light chain CDR1 having an amino acid sequence represented by SEQ ID NO: 26;

(e) a light chain CDR2 having an amino acid sequence represented by SEQ ID NO: 27;

(f) a light chain CDR3 having an amino acid sequence represented by SEQ ID NO: 28;

(g) a CDR having any of the amino acid sequences represented by SEQ ID NOs: 23 to 28 and having therein deletion, substitution, or addition of one or two amino acids; and (h) a CDR having an amino acid sequence having at least 90% homology with any of the amino acid sequences represented by SEQ ID NOs: 23 to 28;

[11] the therapeutic agent or preventive for an inflammatory disease as described above in [1], wherein the TLR9 antibody is any of antibodies described below:

(1) an antibody containing a heavy chain having an amino acid sequence represented by SEQ ID NO: 29 and a light chain having an amino acid sequence represented by SEQ ID NO: 30;

(2) an antibody containing a heavy chain and/or a light chain having the amino acid sequence represented by SEQ ID NO: 29 and/or 30 and having therein deletion, substitution or addition of one or several amino acids; and (3) an antibody containing a heavy chain and/or light chain having an amino acid sequence having at least 70% homology with the amino acid sequence represented by SEQ ID NO: 29 and/or 30;

[12] the therapeutic agent or preventive for an inflammatory disease as described above in [1], wherein the TLR9 antibody is any of antibodies described below:

(1) an antibody containing a heavy chain having an amino acid sequence represented by SEQ ID NO: 31 and a light chain having an amino acid sequence represented by SEQ ID NO: 32;

(2) an antibody containing a heavy chain and/or a light chain having the amino acid sequence represented by SEQ ID NO: 31 and/or 32 and having therein deletion, substitution or addition of one or several amino acids; and (3) an antibody containing a heavy chain and/or light chain having the amino acid sequence having at least 70% homology with the amino acid sequence represented by SEQ ID NO: 31 and/or 32;

[13] the therapeutic agent or preventive for an inflammatory disease as described above in [1], wherein the TLR9 antibody is any of antibodies described below:

(1) an antibody containing a heavy chain having an amino acid sequence represented by SEQ ID NO: 33 and a light chain having an amino acid sequence represented by SEQ ID NO: 34;

(2) an antibody containing a heavy chain and/or a light chain having the amino acid sequence represented by SEQ ID NO: 33 and/or 34 and having therein deletion, substitution or addition of one or several amino acids; and (3) an antibody containing a heavy chain and/or light chain having an amino acid sequence having at least 70% homology with the amino acid sequence represented by SEQ ID NO: 33 and/or 34;

[14] the therapeutic agent or preventive for an inflammatory disease as described above in any one of [1] to [13], wherein the inflammatory disease is an autoimmune disease;

[15] the therapeutic agent or preventive for an inflammatory disease as described above in [14], wherein the autoimmune disease is systemic lupus erythematosus or psoriasis;

[16] any of anti-TLR7 antibodies described below:

(i) an antibody containing at least one of the follow CDRs: (a) a heavy chain CDR1 having an amino acid sequence represented by SEQ ID NO: 3; (b) a heavy chain CDR2 having an amino acid sequence represented by SEQ ID NO: 4; (c) a heavy chain CDR3 having an amino acid sequence represented by SEQ ID NO: 5; (d) a light chain CDR1 having an amino acid sequence represented by SEQ ID NO: 6; (e) a light chain CDR2 having an amino acid sequence represented by SEQ ID NO: 7; (f) a light chain CDR3 having an amino acid sequence represented by SEQ ID NO: 8; (g) a CDR having any of the amino acid sequences represented by SEQ ID NOs: 3 to 8 and having therein deletion, substitution, or addition of one or two amino acids; and (h) a CDR having an amino acid sequence having at least 90% homology with any of the amino acid sequences represented by SEQ ID NOs: 3 to 8;

(ii) any of antibodies described below: (1) an antibody containing a heavy chain having an amino acid sequence represented by SEQ ID NO: 9 and a light chain having an amino acid sequence represented by SEQ ID NO: 10; (2) an antibody containing a heavy chain and/or light chain having the amino acid sequence represented by SEQ ID NO: 9 and/or 10 and having therein deletion, substitution, or addition of one or several amino acids; and (3) a heavy chain and/or light chain having an amino acid sequence having at least 70% homology with the amino acid sequence represented by SEQ ID NO: 9 and/or 10;

(iii) a monoclonal antibody that specifically binds to a region from position 27 to position 457 of an amino acid sequence of TLR7 represented by SEQ ID NO: 1;

(iv) an antibody that specifically binds to a region from position 228 to position 364 of an amino acid sequence of mouse TLR7 represented by SEQ ID NO: 1 or an amino acid sequence of human TLR7 represented by SEQ ID NO: 39;

(v) an antibody that specifically binds to a region including a region from position 275 to position 313 of the amino acid sequence of mouse TLR7 represented by SEQ ID NO: 1 or the amino acid sequence of human TLR7 represented by SEQ ID NO: 39; or (vi) an antibody that specifically binds to a region including a region from position 313 to position 364 of the amino acid sequence of mouse TLR7 represented by SEQ ID NO: 1 or the amino acid sequence of human TLR7 represented by SEQ ID NO: 39; and

[17] any of TLR9 antibodies described below:

(i) an monoclonal antibody containing at least one of the follow CDRs:

(a) a heavy chain CDR1 having an amino acid sequence represented by SEQ ID NO: 11; (b) a heavy chain CDR2 having an amino acid sequence represented by SEQ ID NO: 12; (c) a heavy chain CDR3 having an amino acid sequence represented by SEQ ID NO: 13; (d) a light chain CDR1 having an amino acid sequence represented by SEQ ID NO: 14; (e) a light chain CDR2 having an amino acid sequence represented by SEQ ID NO: 15; (f) a light chain CDR3 having an amino acid sequence represented by SEQ ID NO: 16; (g) a CDR having any of the amino acid sequences represented by SEQ ID NOs: 11 to 16 and having therein deletion, substitution, or addition of one or two amino acids; and (h) a CDR having an amino acid sequence having at least 90% homology with any of the amino acid sequences represented by SEQ ID NOs: 11 to 16;

(ii) a monoclonal antibody containing at least one of CDRs described below; (a) a heavy chain CDR1 having an amino acid sequence represented by SEQ ID NO: 17; (b) a heavy chain CDR2 having an amino acid sequence represented by SEQ ID NO: 18; (c) a heavy chain CDR3 having an amino acid sequence represented by SEQ ID NO: 19; (d) a light chain CDR1 having an amino acid sequence represented by SEQ ID NO: 20; (e) a light chain CDR2 having an amino acid sequence represented by SEQ ID NO: 21; (f) a light chain CDR3 having an amino acid sequence represented by SEQ ID NO: 22; (g) a CDR having any of the amino acid sequences represented by SEQ ID NOs: 17 to 22 and having therein deletion, substitution, or addition of one or two amino acids; and (h) a CDR having an amino acid sequence having at least 90% homology with any of the amino acid sequences represented by SEQ ID NOs: 17 to 22;

(iii) a monoclonal antibody containing at least one of CDRs described below; (a) a heavy chain CDR1 having an amino acid sequence represented by SEQ ID NO: 23; (b) a heavy chain CDR2 having an amino acid sequence represented by SEQ ID NO: 24; (c) a heavy chain CDR3 having an amino acid sequence represented by SEQ ID NO: 25; (d) a light chain CDR1 having an amino acid sequence represented by SEQ ID NO: 26; (e) a light chain CDR2 having an amino acid sequence represented by SEQ ID NO: 27; (f) a light chain CDR3 having an amino acid sequence represented by SEQ ID NO: 28; (g) a CDR having any of the amino acid sequences represented by SEQ ID NOs: 23 to 28 and having therein deletion, substitution, or addition of one or two amino acids; and (h) a CDR having an amino acid sequence having at least 90% homology with any of the amino acid sequences represented by SEQ ID NOs: from 23 to 28;

(iv) any of antibodies described below: (1) an antibody containing a heavy chain having an amino acid sequence represented by SEQ ID NO: 29 and a light chain having an amino acid sequence represented by SEQ ID NO: 30; (2) an antibody containing a heavy chain and/or light chain having the amino acid sequence represented by SEQ ID NO: 29 and/or 30 and having therein deletion, substitution or addition of one or several amino acids; and (3) an antibody containing a heavy chain and/or light chain having an amino acid sequence having at least 70% homology with the amino acid sequence represented by SEQ ID NO: 29 and/or 30;

(v) any of antibodies described below: (1) an antibody containing a heavy chain having an amino acid sequence represented by SEQ ID NO: 31 and a light chain having an amino acid sequence represented by SEQ ID NO: 32; (2) an antibody containing a heavy chain and/or a light chain having the amino acid sequence represented by SEQ ID NO: 31 and/or 32 and having therein deletion, substitution or addition of one or several amino acids; and (3) an antibody containing a heavy chain and/or light chain having an amino acid sequence having at least 70% homology with the amino acid sequence represented by SEQ ID NO: 31 and/or 32; or (vi) any of antibodies described below: (1) an antibody containing a heavy chain having an amino acid sequence represented by SEQ ID NO: 33 and a light chain having an amino acid sequence represented by SEQ ID NO: 34, (2) an antibody containing a heavy chain and/or a light chain having an amino acid sequence represented by SEQ ID NO: 33 and/or 34 and having therein deletion, substitution, or addition of one or several amino acids; and (3) a heavy chain and/or a light chain containing an amino acid sequence having at least 70% homology with the amino acid sequence represented by SEQ ID NO: 33 and/or 34.

Effect of the Invention

The present invention makes it possible to prevent or treat inflammatory diseases by specifically inhibiting the function of a cell surface TLR7 or TLR9. The preventive or therapeutic agent for inflammatory diseases according to the present invention has an anti-TLR7 antibody or an anti-TLR9 antibody as an effective component so that in addition, it is presumed to be highly safe.

BRIEF DESCRIPTION OF THE DRAWINGS

FIG. 7B shows the results of causing TLR9-GFP to express in B cell lymphoma line M12 (lane 1) or PRAT4A silenced M12 (lane 2), immunoprecipitating it, and detecting it using an anti-GFP antibody. The term "TLR9F" means full-length TLR9 and the term "TLR9C" means a TLR9 fragment on the C-terminal side after processing. The symbol * shows a non-specific band.

FIG. 7C shows, with an arrow, an N-terminal amino acid of a fragment found by N-terminal amino acid sequence analysis of TLR9C. A human TLR9 amino acid sequence corresponding to it is also shown. The fragment of mouse TLR9 has an amino acid of SEQ ID NO: 40; the corresponding fragment of human TLR9 has an amino acid of SEQ ID NO: 41.

FIG. 7D is a schematic view showing a cleavage site in the TLR9 ectodomain. The term "LRR" means a leucine-rich repeat.

FIG. 7E shows the results of preparing Ba/F3 cells expressing HA epitope, TLR9 ectodomain (TLR9F, TLR9N, or TLR9C), and a membrane permeation site and subjecting them to membrane permeability staining with an anti-TLR9 antibody or anti-HA epitope antibody. Black histograms show the results of staining with only a secondary reagent. Experiment was repeated three times and typical data are shown in this drawing.

Figure 1A:
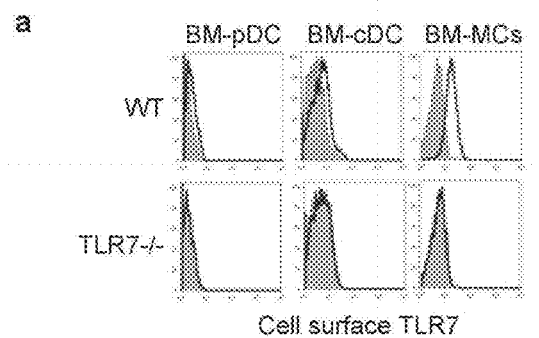
FIG. 1A shows the results of measuring the cell surface TLR7 in various cells through flow cytometry. White histograms show the cell surface TLR7 in bone marrow-derived plasmacytoid dendritic cells (BM-pDCs), classical dendritic cells (BM-cDCs), and macrophages (BM-MCs). TLR7$^{-/-}$ cells were stained as a negative control. Gray histograms show the staining with only a secondary reagent.

FIG. 8A shows the results of staining Ba/F3 cells expressing only TLR9 or TLR9 and Unc93B1 with three kinds of anti-TLR9 monoclonal antibodies (C34A1, B33A4, and J15A7). Staining of the cell surface is shown in the upper side and membrane permeability staining is shown in the lower side.

FIG. 8B shows the results of staining spleen cells derived from the wild type mice, Unc93B1$^{3d/3d}$ mice or Tlr9$^{-/-}$ mice with an anti-TLR9 monoclonal antibody J15A7 and mAb against DC marker shown in the drawing. Gray histograms show staining with a secondary reagent. Experiment was repeated twice and typical data are shown in the drawing.

FIG. 9A is a schematic view showing a cleavage site in a TLR7 ectodomain. The term "LRR" shows a leucine-rich repeat. The mTLR7 has an amino acid sequence of SEQ ID NO: 42.

FIG. 9B shows the results of studying the binding of an A94B10 antibody to TLR7N, TLR7C, or TLR7F.

Figure 10:
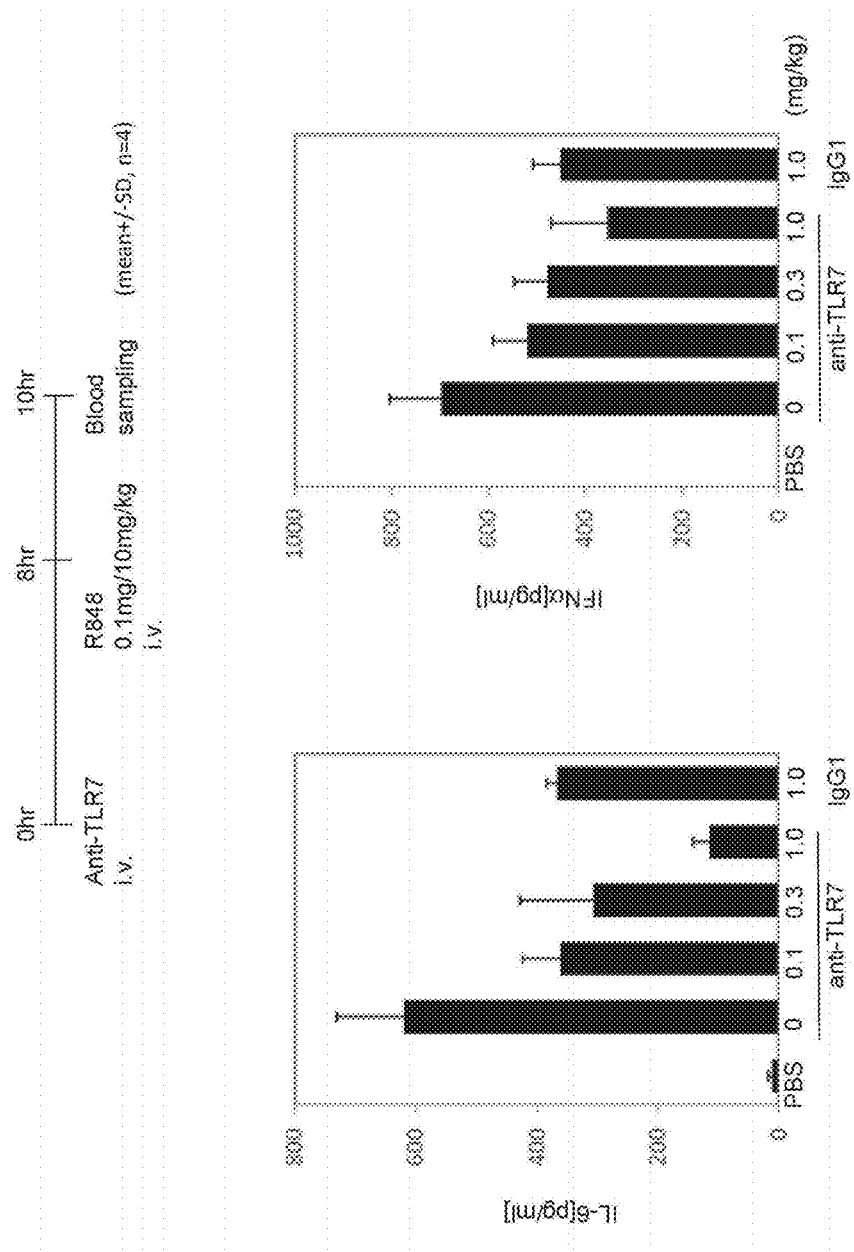

FIG. 10 shows the results of administering an A94B10 antibody to mice and at the same time administering R848 which is a TLR7 ligand to induce inducing inflammatory cytokine production and studying the suppression of inflammatory cytokine production by the A94B10 antibody.

Figure 11:
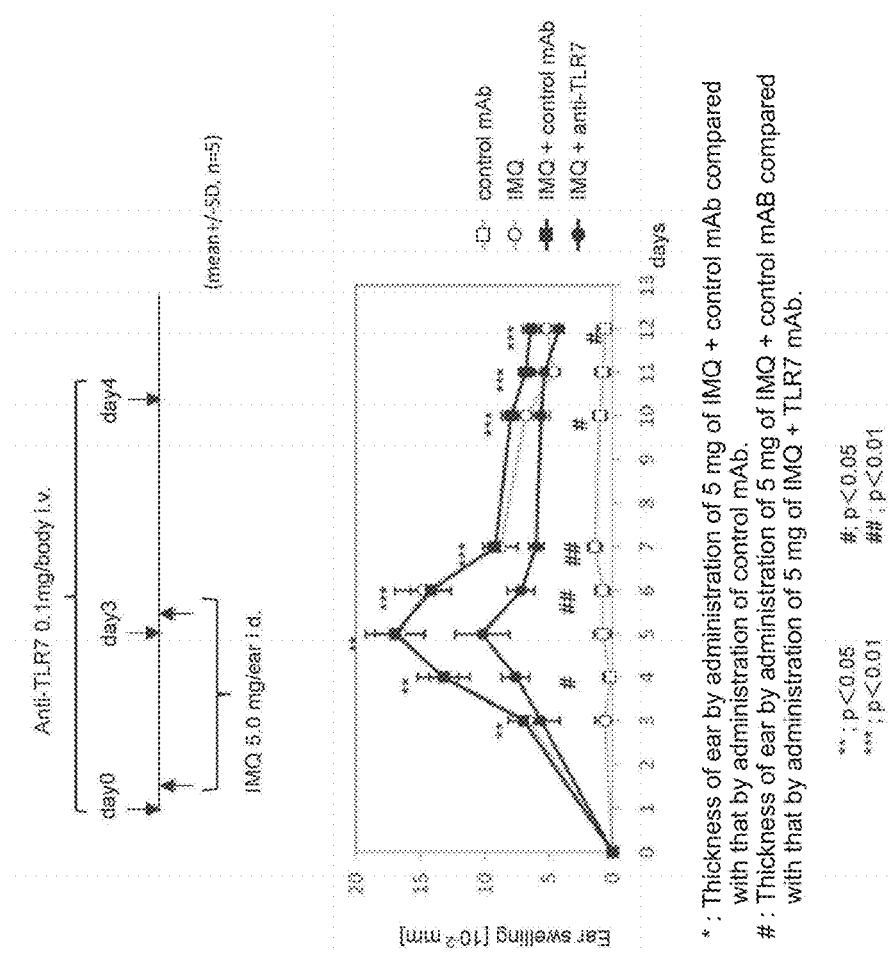

FIG. 11 shows the results of administering an A94B10 antibody to mice and at the same time administering Imiquimod which is a TLR7 ligand to the ear of the mice to induce inflammation of the skin and studying the suppression of inflammation by the A94B10 antibody.

Figure 12:
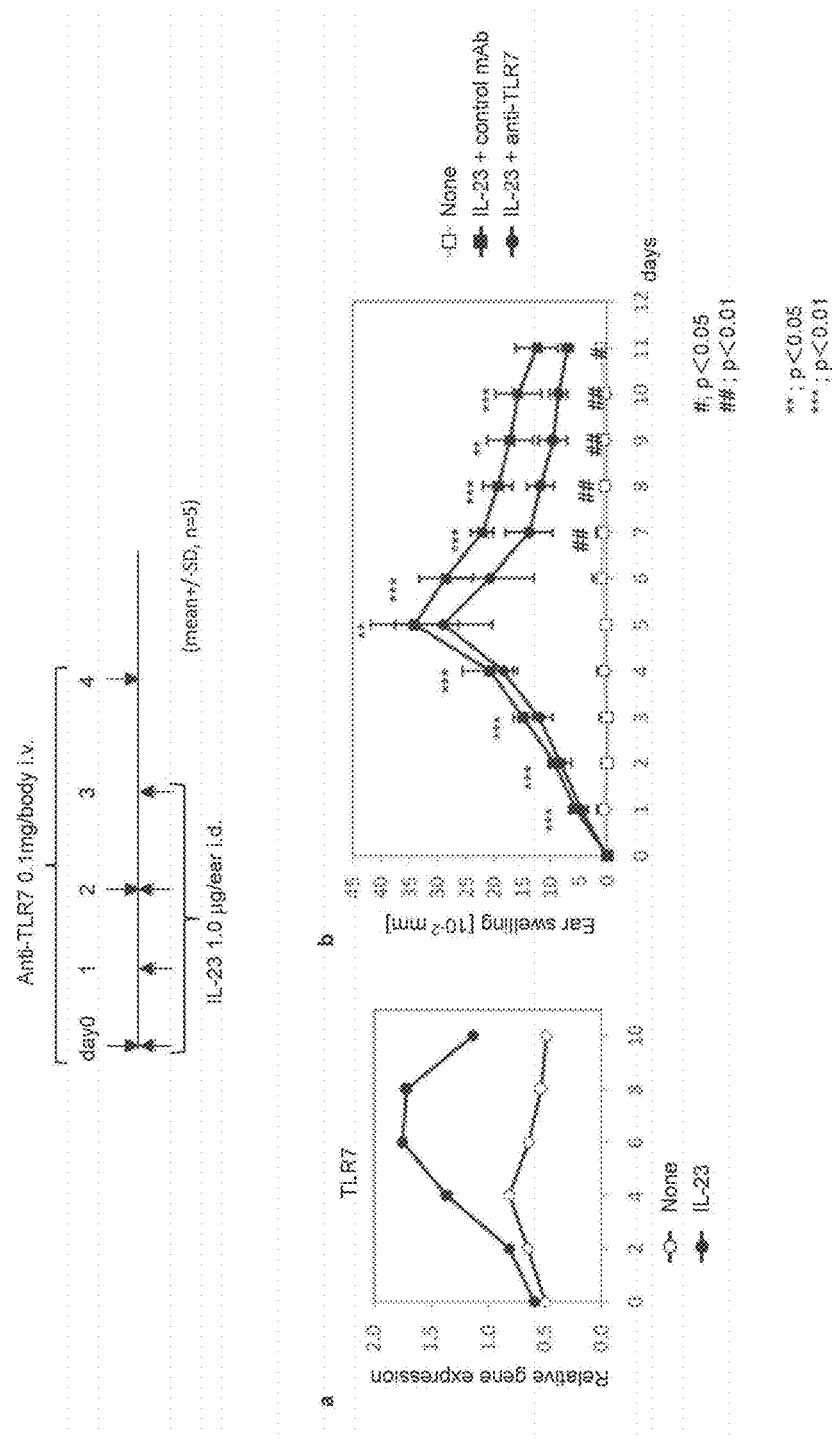

FIG. 12 shows the results of administering IL-23 to the ear of mice to prepare a psoriasis mouse model and at the same time administering an A94B10 antibody and then studying the suppression of inflammation by the A94B10 antibody.

FIG. 13 shows the results of preparing a TLR7 fragment and studying the binding of an A94B10 antibody to the fragment and thereby analyzing the epitope of the A94B10 antibody. The TLR7 fragment has an amino acid sequence of SEQ ID NO: 43.

Figure 14:
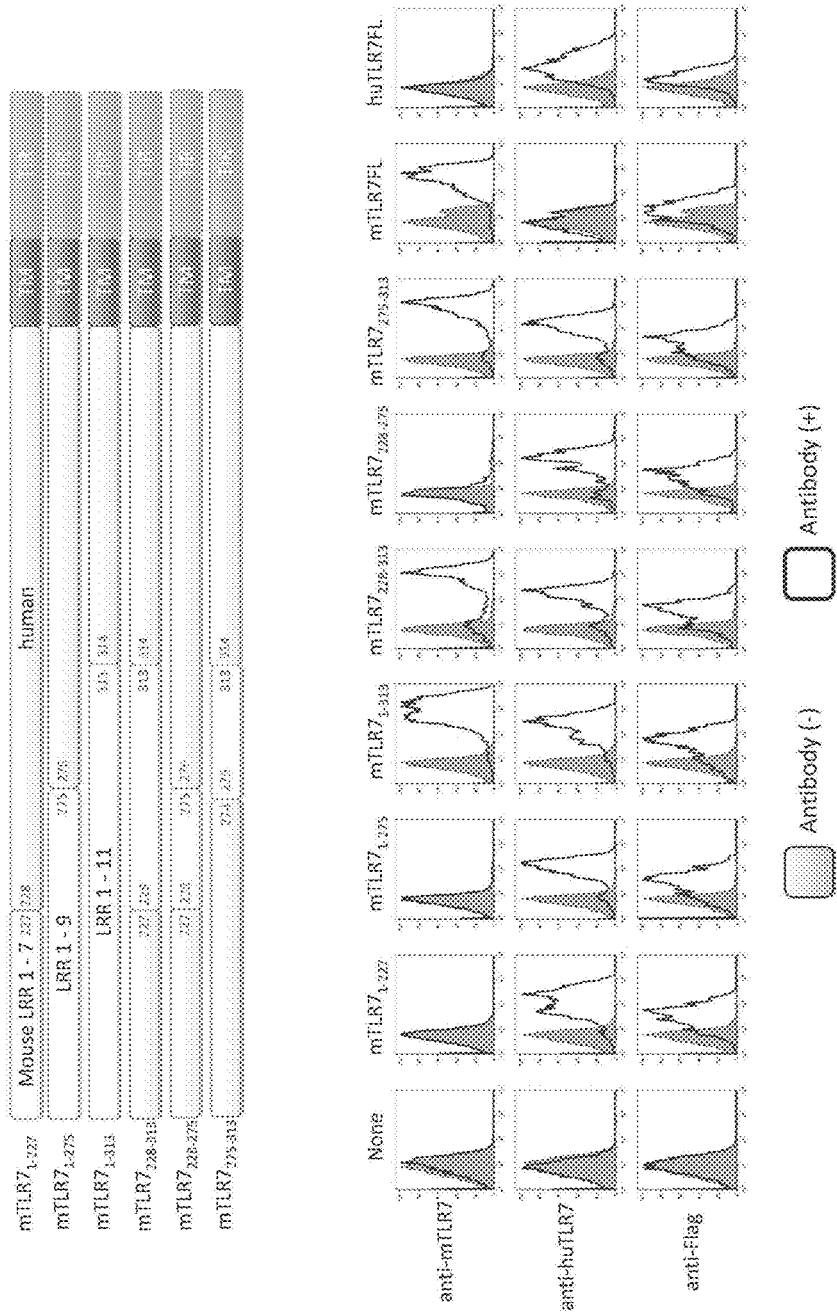

FIG. 14 shows the results of preparing chimeric TLR7 of mouse TLR7 and human TLR7 and studying the binding of an A94B10 antibody to the chimeric TLR7 and thereby analyzing the epitope of the A94B10 antibody.

MODE FOR CARRYING OUT THE INVENTION

[Therapeutic Agent or Preventive for Inflammatory Diseases]

A therapeutic agent or preventive for inflammatory diseases according to the present invention contains an anti-TLR7 antibody or an anti-TLR9 antibody.

The murine TLR family consists of 12 members, while the human TLR family consists of 10 members. TLR1, TLR2, TLR4, TLR5, and TLR6 are distributed in the cell surface and recognize a lipoprotein which is a bacterial membrane component, a glycolipid such as LPS, or a protein such as flagellin. TLR3, TLR7, TLR8, and TLR9 are distributed in an endoplasmic reticulum which is an intracellular organelle and recognize a nucleic acid derived from bacteria or viruses.

TLR is a type I membrane protein with an extracellular leucine-rich repeat (LRR). Recognizing a pathogenic component, it transduces signals through the intracellular Toll/IL-1R homology (TIR) domain. The TLR that has recognized a ligand transduces signals to cells via the TIR domain to activate transcription factors such as NF—κB and Interferon-Regulatory Factor (IRF) family, induce production of inflammatory cytokines (such as IL-6, IL-12, and TNFα), inflammatory chemokines (such as RANTES), or type I interferon (IFNα or IFNβ), and regionally cause appropriate innate immune response. The immune response via these TLRs is indispensable in biophylaxis. It is reported that lack of molecules associated with TLR response is likely to cause infection to various pathogens. It is however reported that when an autologous substance becomes an endogenic ligand of TLRs because of some reasons, it may cause chronic inflammation.

In fact, TLR7 is known to be involved in the onset of SLE or psoriasis.

An anti-TLR7 antibody, as shown in Examples described later, binds to the cell surface TLR7, inhibits TLR7 response of the cells, prevents abnormal immunological activation, and thereby contributes to treatment or prevention of inflammatory diseases. TLR7 is a type I membrane protein having an amino acid sequence represented by SEQ ID NO: 1.

Similar to TLR7, TLR9 is also known to be involved in the disease condition of psoriasis. An anti-TLR9 antibody is presumed to bind to the cell surface TLR9, inhibit TLR9 response of the cells, prevent abnormal immunological activation, and thereby contribute to treatment or prevention of inflammatory diseases.

TLR9 is a type I membrane protein having an amino acid sequence represented by SEQ ID NO: 2.

(Anti-TLR7 Antibody)

In one mode, the anti-TLR7 antibody to be used in the present invention contains at least one of CDRs described below:

(a) a heavy chain CDR1 having an amino acid sequence represented by SEQ ID NO: 3;

(b) a heavy chain CDR2 having an amino acid sequence represented by SEQ ID NO: 4;

(c) a heavy chain CDR3 having an amino acid sequence represented by SEQ ID NO: 5;

(d) a light chain CDR1 having an amino acid sequence represented by SEQ ID NO: 6;

(e) a light chain CDR2 having an amino acid sequence represented by SEQ ID NO: 7;

(f) a light chain CDR3 having an amino acid sequence represented by SEQ ID NO: 8;

(g) a CDR having any of the amino acid sequences represented by SEQ ID NOs: 3 to 8 and having therein deletion, substitution, or addition of one or two amino acids; and (h) a CDR having an amino acid sequence having at least 90% homology with any one of the amino acid sequences represented by SEQ ID NOs: 3 to 8;

The anti-TLR7 antibody to be used in the present invention may be an antibody containing at least two, at least three, at least four, at least five or all of the heavy chains CDR1 to 3 and light chains CDR1 to 3 described above in (a) to (f).

The antibodies having any of the CDRs having an amino acid sequence represented by SEQ ID NOS: 3 to 8 inhibit TLR7 response in immune cells and improve the disease condition of an inflammatory disease mouse model as shown in Examples.

In the anti-TLR7 antibody to be used in the present invention, at least one of the heavy chains CDR1 to 3 and the light chains CDR 1 to 3 described above in (a) to (f) may have, in the amino acid sequence thereof, deletion, substitution, or addition of one or two amino acids.

The term "amino acid" is used herein in its broadest meaning and embraces not only a natural amino acid but also an unnatural amino acid such as amino acid variant or derivative. Examples of the amino acid include, but not limited to, natural proteinaceous L-amino acids; D-amino acids; chemically modified amino acids such as amino acid variants and derivatives; natural nonproteinaceous amino acids such as nerleucine, β-alanine, and ornithine; and chemically synthesized compounds having properties characteristic to amino acids and known per se in the art. Examples of the unnatural amino acids include, but not limited to, α-methylamino acids (such as α-methylalanine), D-amino acids, histidine-like amino acids (such as 2-aminohistidine, β-hydroxy-histidine, homohistidine, α-fluoromethyl-histidine, and α-methyl-histidine), amino acids having, in the side chain thereof, excess methylene (such as "homo" amino acid), and amino acids obtained by substituting, with a sulfonic acid group, an amino acid (such as cysteic acid) having a carboxylic acid functional group in the side chain thereof.

In the case of "having deletion, substitution, or addition of one or two amino acids" as described herein, the number of amino acids which are deleted, substituted, or the like is not particularly limited insofar as the set of the CDRs available as a result maintains its antigen recognition function. The position of deletion, substitution, or addition in each CDR may be any of at N terminal, at C terminal, or between them insofar as the set of the CDRs available as a result maintains its antigen recognition function.

In the anti-TLR7 antibody to be used in the present invention, at least one of the heavy chains CDR 1 to 3 and the light chains CDR 1 to 3 described above in (a) to (f) may have an amino acid sequence having at least 90% homology with the amino acid sequence represented by SEQ ID NOs: 3 to 8.

The term "having at least Y % homology with an amino acid sequence represented by SEQ ID NO: X" as used herein means that when two polypeptides are arranged (aligned) to give the maximum coincidence of their amino acid sequences, a proportion of the number of amino acid residues in common is at least Y % based on the total number of amino acids of SEQ ID NO: X.

The anti-TLR7 antibody to be used in the present invention may have an amino acid sequence having at least 90%, at least 95%, or at least 98% homology with the amino acid sequence represented by SEQ ID NOs: 3 to 8 insofar as the set of the CDRs available as a result can maintain their function as a CDR of the anti-TLR7 antibody.

The anti-TLR7 antibody to be used in the present invention may any of the following antibodies:

(1) an antibody containing a heavy chain containing an amino acid sequence represented by SEQ ID NO: 9 and a light chain containing an amino acid sequence represented by SEQ ID NO: 10;

(2) an antibody containing a heavy chain and/or a light chain having an amino acid sequence represented by an amino acid sequence SEQ ID NO: 9 and/or 10 and having therein an amino acid sequence with deletion, substitution or addition of one or several amino acids;

(3) an antibody containing a heavy chain and/or light chain having an amino acid sequence having at least 70% homology with the amino acid sequence represented by SEQ ID NO: 9 and/or 10; and (4) an antibody that recognizes an epitope similar to that recognized by any of the antibodies described in (1) to (3).

The terms "an antibody containing a heavy chain and/or a light chain having an amino acid sequence represented by SEQ ID NO: 9 and/or 10 and having therein deletion, substitution or addition of one or several amino acids" as used herein mean that the heavy chain has an amino acid sequence represented by SEQ ID NO: 9 and has therein deletion, substitution, or addition of one or several amino acids; and/or the light chain has an amino acid sequence represented by SEQ ID NO: 10 and has therein deletion, substitution, or addition of one or several amino acids. The number of amino acids deleted, substituted, or added is not particularly limited insofar as the resulting antibody containing the heavy chain and the light chain specifically binds to TLR9 and the number can be set at, for example, 1, 2, 3, 4, 5, 6, 7, 8, 9, or 10. Also the position of deletion, substitution, or addition is not particularly limited insofar as the resulting antibody containing the heavy chain and the light chain specifically binds to TLR9. This similarly applies to SEQ ID NOs: 29 to 34 which will be described later.

The terms "antibody containing a heavy chain and/or a light chain having an amino acid sequence having at least 70% homology with the amino acid sequence represented by SEQ ID NO: 29 and/or 30" as used herein mean that the heavy chain has at least 70% homology with the amino acid sequence represented by SEQ ID NO: 29 and/or the light chain has at least 70% homology with the amino acid sequence represented by SEQ ID NO: 30. Although homology is not particularly limited insofar as the resulting antibody containing the heavy chain and the light chain specifically binds to TLR9, examples include at least 80%, at least 85%, at least 90%, at least 95%, and at least 98%. This similarly applies to SEQ ID NOs: 29 to 34 which will be described later.

The amino acid sequence represented by SEQ ID No: 9 is an amino acid sequence of a heavy chain of an A94B10 antibody which will be shown later in Examples and the amino acid sequence represented by SEQ ID NO: 10 is an amino acid sequence of a light chain of the A94B10 antibody.

The antibodies shown above in (1) to (4), similar to the A94B10 antibody, are therefore presumed to inhibit TLR7 response in immune cells.

The anti-TLR7 antibody to be used in the present invention may bind to a region (which may hereinafter be called "TLR7N") from position 27 to position 457 of the amino acid sequence of TLR7 represented by SEQ ID NO: 1. As shown in Examples, the anti-TLR7 antibody binding to this region inhibits TLR7 response in immune cells.

The anti-TLR7 antibody to be used in the present invention may bind to a region (which may hereinafter be called "TLR7N") from position 228 to position 364 of the amino acid sequence of mouse TLR7 represented by SEQ ID NO: 1. As shown in Examples, the anti-TLR7 antibody binding to this region inhibits TLR7 response in immune cells.

The anti-TLR7 antibody to be used in the present invention may bind to a region including a region from position 275 to position 313 of the amino acid sequence of mouse TLR7 represented by SEQ ID NO: 1. As shown in Examples, the anti-TLR7 antibody binding to this region inhibits TLR7 response in immune cells.

The region including the region from position 275 to position 313 of the amino acid sequence of mouse TLR7 represented by SEQ ID NO: 1 may be, for example, a region of 120 amino acids or less, a region of 110 amino acids or less, a region of 100 amino acids or less, or a region of 90 amino acids or less, each including the region from position 275 to position 313.

The anti-TLR7 antibody to be used in the present invention may bind to a region including a region from position 313 to position 364 of the amino acid sequence of mouse TLR7 represented by SEQ ID NO: 1. As shown in Examples, the anti-TLR7 antibody binding to this region inhibits TLR7 response in immune cells.

The region including the region from position 313 to position 364 of the amino acid sequence of mouse TLR7 represented by SEQ ID NO: 1 may be, for example, a region of 120 amino acids or less, a region of 110 amino acids or less, a region of 100 amino acids or less, a region of 90 amino acids or less, a region of 80 amino acids or less, a region of 70 amino acids or less, or a region of 60 amino acids or less, each including the region from position 313 to position 364.

The anti-TLR7 antibody to be used in the present invention may bind to a region from position 228 to position 364 of the amino acid sequence of human TLR7 represented by SEQ ID NO: 39. The anti-TLR7 antibody to be used in the present invention may bind to a region including a region from position 275 to position 313 of the amino acid sequence of human TLR7 represented by SEQ ID NO: 39. The anti-TLR7 antibody to be used in the present invention may bind to a region including a region from position 313 to position 364 of the amino acid sequence of human TLR7 represented by SEQ ID NO: 39. It is known that the human TLR7 has high sequence homology with the mouse TLR7.

(Anti-TLR9 Antibody)

Expression and terms used in the description of the anti-TLR7 antibody will have the same meaning also in the description of the anti-TLR9 antibody unless otherwise particularly specified.

The anti-TLR9 antibody to be used in the present invention may include at least one of CDRs described below.

(a) a heavy chain CDR1 having an amino acid sequence represented by SEQ ID NO: 11;
(b) a heavy chain CDR2 having an amino acid sequence represented by SEQ ID NO: 12;
(c) a heavy chain CDR3 having an amino acid sequence represented by SEQ ID NO: 13;
(d) a light chain CDR1 having an amino acid sequence represented by SEQ ID NO: 14;
(e) a light chain CDR2 having an amino acid sequence represented by SEQ ID NO: 15;
(f) a light chain CDR3 having an amino acid sequence represented by SEQ ID NO: 16;
(g) a CDR having any of the amino acid sequences represented by SEQ ID NOs: 11 to 16 and having therein deletion, substitution, or addition of one or two amino acids; and
(h) a CDR having an amino acid sequence having at least 90% homology with any one of the amino acid sequences represented by SEQ ID NOs: 11 to 16.

The CDRs described above in (a) to (f) are six CDRs of a J15A7 antibody shown in Examples.

The anti-TLR9 antibody to be used in the present invention may include at least one of CDRs described below:

(a) a heavy chain CDR1 having an amino acid sequence represented by SEQ ID NO: 17;
(b) a heavy chain CDR2 having an amino acid sequence represented by SEQ ID NO: 18;
(c) a heavy chain CDR3 having an amino acid sequence represented by SEQ ID NO: 19;
(d) a light chain CDR1 having an amino acid sequence represented by SEQ ID NO: 20;
(e) a light chain CDR2 having an amino acid sequence represented by SEQ ID NO: 21;
(f) a light chain CDR3 having an amino acid sequence represented by SEQ ID NO: 22;
(g) a CDR having any of the amino acid sequences represented by SEQ ID NOs: 17 to 22 and having therein deletion, substitution, or addition of one or two amino acids; and
(h) a CDR having an amino acid sequence having at least 90% homology with any of the amino acid sequences represented by SEQ ID NOs: 17 to 22.

The CDRs described above in (a) to (f) are six CDRs of a B33A4 antibody shown in Examples.

The anti-TLR9 antibody to be used in the present invention may include at least one of CDRs described below:

(a) a heavy chain CDR1 having an amino acid sequence represented by SEQ ID NO: 23;
(b) a heavy chain CDR2 having an amino acid sequence represented by SEQ ID NO: 24;
(c) a heavy chain CDR3 having an amino acid sequence represented by SEQ ID NO: 25;
(d) a light chain CDR1 having an amino acid sequence represented by SEQ ID NO: 26;
(e) a light chain CDR2 having an amino acid sequence represented by SEQ ID NO: 27;
(f) a light chain CDR3 having an amino acid sequence represented by SEQ ID NO: 28;
(g) a CDR having any of the amino acid sequences represented by SEQ ID NOs: 23 to 28 and having therein deletion, substitution, or addition of one or two amino acids; and
(h) a CDR having an amino acid sequence having at least 90% homology with any of the amino acid sequences represented by SEQ ID NOs: 23 to 28.

The CDRs described above in (a) to (f) are six CDRs of a C34A1 antibody shown in Examples.

The anti-TLR9 antibody to be used in the present invention may be any one of the following antibodies insofar as it binds to a cell surface anti-TLR9:

(1) an antibody containing a heavy chain having an amino acid sequence represented by SEQ ID NO: 29 and a light chain having an amino acid sequence represented by SEQ ID NO: 30;
(2) an antibody containing a heavy chain and/or a light chain having the amino acid sequence represented by SEQ ID NO: 29 and/or 30 and having therein deletion, substitution or addition of one or several amino acids; and
(3) an antibody containing a heavy chain and/or light chain having an amino acid sequence having at least 70% homology with the amino acid sequence represented by SEQ ID NO: 29 and/or 30; and
(4) an antibody that recognizes an epitope similar to that recognized by any of the antibodies described in (1) to (3).

The antibody containing a heavy chain having an amino acid sequence represented by SEQ ID NO: 29 and a light chain having an amino acid sequence represented by SEQ ID NO: 30 is a J15A7 antibody.

The anti-TLR9 antibody to be used in the present invention may be any of the following antibodies insofar as it binds to a cell surface anti-TLR9:

(1) an antibody containing a heavy chain having an amino acid sequence represented by SEQ ID NO: 31 and a light chain having an amino acid sequence represented by SEQ ID NO: 32;
(2) an antibody containing a heavy chain and/or a light chain having the amino acid sequence represented by SEQ ID NO: 31 and/or 32 and having therein deletion, substitution or addition of one or several amino acids;

(3) an antibody containing a heavy chain and/or light chain having an amino acid sequence having at least 70% homology with the amino acid sequence represented by SEQ ID NO: 31 and/or 32; and (4) an antibody that recognizes an epitope similar to that recognized by any of the antibodies described in (1) to (3).

The antibody containing a heavy chain having an amino acid sequence represented by SEQ ID NO: 31 and a light chain having an amino acid sequence represented by SEQ ID NO: 32 is a B33A4 antibody.

The anti-TLR9 antibody to be used in the present invention may be any of the following antibodies insofar as it binds to a cell surface anti-TLR9:

(1) an antibody containing a heavy chain having an amino acid sequence represented by SEQ ID NO: 33 and a light chain having an amino acid sequence represented by SEQ ID NO: 34;

(2) an antibody containing a heavy chain and/or a light chain having an amino acid sequence represented by SEQ ID NO: 33 and/or 34 and having therein deletion, substitution or addition of one or several amino acids; and (3) an antibody containing a heavy chain and/or light chain having an amino acid sequence having at least 70% homology with the amino acid sequence represented by SEQ ID NO: 33 and/or 34; and (4) an antibody that recognizes an epitope similar to that recognized by any of the antibodies described in (1) to (3).

The antibody containing a heavy chain having an amino acid sequence represented by SEQ ID NO: 33 and a light chain having an amino acid sequence represented by SEQ ID NO: 34 is a C34A1 antibody.

The anti-TLR7 antibody and the anti-TLR9 antibody to be used in the present invention may each be a monoclonal antibody or a polyclonal antibody. The anti-TLR7 antibody and the anti-TLR9 antibody to be used in the present invention may be any of isotypes IgG, IgM, IgA, IgD, and IgE.

The anti-TLR7 antibody and the anti-TLR9 antibody to be used in the present invention may be a mouse antibody, a human CDR-grafted antibody, a human chimeric antibody, a humanized antibody, or a fully human antibody or they may be a low molecular antibody insofar as they bind to cell surface TLR7 and TLR9, respectively, and inhibit their function. They are however not limited to the above-described ones.

The human CDR-grafted antibody is an antibody obtained by substituting a CDR of a non-human animal antibody with a CDR of a human antibody. The human chimeric antibody is an antibody composed of a variable region derived from a non-human animal antibody and a constant region derived from a human antibody. The humanized antibody is an antibody obtained by incorporating a portion derived from a human antibody while leaving a highly-safe partial region of a non-human animal antibody. It is a concept embracing a human chimeric antibody or a human CDR-grafted antibody.

The term "low-molecular antibody" as used herein means a fragment of an antibody or a fragment of an antibody having an arbitrary molecule bound thereto that recognizes an epitope similar to that recognized by the original antibody. Specific examples include, but not limited to, Fab composed of VL, VH, CL, and CH1 regions, F(ab')2 in which two Fabs have been linked to each other via a disulfide bond in the hinge region, Fv composed of VL and VH; and scFV which is a single-stranded antibody in which VL and VH have been linked to each other via an artificial polypeptide linker and include, in addition, sdFv, Diabody, and sc(Fv)2.

[Antibody]

The present invention also provides an anti-TLR7 antibody or an anti-TLR9 antibody itself contained in the above-described therapeutic agent or preventive for inflammatory diseases.

[Preparation Process of Antibody]

Although a preparation process of the anti-TLR7 antibody or anti-TLR9 antibody to be used in the present invention is not limited, an anti-TLR7 monoclonal antibody can be obtained, for example, by isolating antibody producting cells from a non-human mammal immunized with TLR7 or a fragment thereof, fusing them with myeloma cells or the like to prepare hybridomas, and purifying an antibody produced by these hybridomas. An anti-TLR7 polyclonal antibody can be obtained from the serum of an animal immunized with TLR7 or a fragment thereof. Although the fragment of TLR7 used for immunization is not particularly limited insofar as the antibody thus obtained binds to the cell surface TLR7 and inhibits its function, examples include a TLR7 fragment of SEQ ID NO: 1 having from the 27-th amino acid to the 457-th amino acid.

The anti-TLR9 monoclonal antibody or polyclonal antibody can be prepared similarly.

When an anti-TLR7 antibody having a specific amino acid sequence is prepared, the anti-TLR7 antibody can be prepared, for example, by transforming a proper host with an expression vector containing a nucleic acid encoding the anti-TLR7 antibody, incubating the resulting transformant under appropriate conditions to express an antibody, and then isolating and purifying it in a known manner. The antibody can be isolated and purified, for example, by affinity column using protein A or the like, another chromatography column, filter, ultrafiltration, salting-out, or dialysis. They can be combined as needed. An anti-TLR9 antibody can also be prepared similarly.

The "antibody Y specifically binding to an epitope similar to that recognized by a certain antibody X" can be prepared after determination of the sequence of the epitope as follows.

For example, an epitope on an antigen protein can be determined by immobilizing many peptides having a random sequence to a solid-phase carrier to form an array, causing it to react with the antibody X, detecting binding while using an enzyme-labeled secondary antibody, studying the amino acid sequence of the peptide to which the antibody X specifically binds, and retrieving homology between this amino acid sequence and the amino acid sequence of the antigen protein. As the peptides immobilized onto a solid-phase carrier, a group of partial peptides of an antigen protein may be used.

Alternatively, an epitope on an antigen protein may be determined by detecting binding, in the presence of various partial peptides of the antigen protein, between the antibody X and the antigen protein by the ELISA method and determining the presence or absence of competitive activity.

When the sequence of the epitope can be determined, an antibody Y specifically binding to it can be prepared by those skilled in the art in a known manner. For example, an antibody specifically binding to the epitope can be obtained by immobilizing a peptide containing the epitope sequence to a solid-phase carrier and detecting binding between the peptide and various antibodies.

As "various antibodies", those obtained by immunizing an animal with an antigen protein or a partial peptide thereof may be used or an antibody library or an antibody fragment library prepared by phage display method may be used. When a library prepared by phage display method is used, an antibody Y specifically binding to the epitope can be obtained by immobilizing a peptide containing the sequence of the epitope onto a solid phase carrier and repeating the panning.

A human chimeric antibody and a human CDR-grafted antibody can be prepared by cloning an antibody gene from the mRNA of a hybridoma that produces a non-human animal antibody and linking it with a portion of a human antibody gene through gene recombination technique.

For example, a human chimeric antibody can be obtained as follows. From the mRNA of a hybridoma that produces a mouse antibody, cDNA is synthesized using a reverse transcriptase. A heavy chain variable region (VH) and a light chain variable region (LH) are cloned by PCR and the sequence is analyzed. Next, a 5' primer containing a leader sequence is prepared from an antibody base sequence having a high coincidence ratio and the above-described cDNA from a signal sequence to the 3' end of the variable region is cloned with the 5' primer and variable 3' primer using PCR. On the other hand, the constant region of the heavy chain and the light chain of human IgG1 is cloned and for each of the heavy chain and the light chain, the mouse antibody-derived variable region and the human antibody-derived constant region are linked to each other and amplified by the overlapping hanging method by PCR. The DNA thus obtained was inserted into an appropriate vector, followed by transformation to obtain a human chimeric antibody.

In the case of the CDR-grafted antibody, a human antibody variable portion having highest homology with a mouse antibody variable portion to be used is selected and cloned and the base sequence of the CDR is altered by site-selective mutation introduction by using the mega primer method. If humanization of an amino acid sequence constituting a framework region makes the specific binding with an antigen impossible, the amino acid of a portion of the framework may be converted from a human type to a rat type.

The "CDR having an amino acid sequence represented by SEQ ID NO: X and having therein deletion, substitution, or addition of one or two amino acids" or the "CDR having an amino acid sequence at least Y % homology with an amino acid sequence represented by SEQ ID NO: X" can be prepared by a known method such as site-specific mutagenesis, random mutagenesis, chain shuffling, or CDR walking.

It is known to those skilled in the art that a CDR having more mature affinity can be obtained by displaying an antibody having in CDR thereof various mutations or a fragment of the antibody on a phage surface by a phage display method and screening them using an antigen (for example, Wu et al., PNAS, 95:6037-6042(1998); Schier, R. et al., J. Mol. Bio. 263:551-567(1996); Schier, R. et al., J. Mol. Biol. 255:28-43(1996); Yang, W. P. et al., J. Mol. Biol., 254:392-403(1995)). The present invention embraces an antibody containing a CDR matured by such a method.

Examples of another antibody preparation process include the Adlib method (Seo, H. et al., Nat. Biotechnol., 6:731-736, 2002) in which an antibody producing strain is obtained from a DT40 cell line derived from the trichostatin A-treated chicken B cells and a method of immunizing a KM mice, which are mice having a human antibody gene introduced therein instead of a disrupted mouse antibody gene, and preparing a human antibody (Itoh, K. et al., Jpn. J. Cancer Res., 92:1313-1321, 2001; Koide, A. et al., J. Mol. Biol., 284:1141-1151, 1998). These methods can also be applied to antibody production in the present invention.

When the anti-TLR7 antibody or anti-TLR9 of the present invention antibody is a low molecular antibody, it may be expressed by the above-described method while using a DNA encoding this low-molecular antibody. Alternatively, it may be prepared by treating a full-length antibody with an enzyme such as papain or pepsin.

Antibodies to be used in the present invention may be different in amino acid sequence, molecular weight, isoelectric point, presence or absence of sugar chain, shape, or the like. Even so, these antibodies are embraced in the present invention insofar as they have a function equivalent to that of the antibody of the present invention. For example, when the antibody of the present invention is expressed using prokaryotic cells such as *Escherichia coli*, it has, at the N terminal of the amino acid sequence of the original antibody, a methionine residue. Such an antibody is also embraced in the present invention.

[Preventive or Therapeutic Agent]

Those skilled in the art can determine as needed whether or not the anti-TLR7 antibody or anti-TLR9 antibody can be used for the preventive or therapeutic agent for inflammatory diseases according to the present invention.

For example, it is possible to select, from the resulting antibodies, those usable as a preventive or therapeutic agent for autoimmune diseases by confirming, according to the process shown in Example, at least one of (i) whether or not the resulting antibody binds to the cell surface TLR7 or TLR9; (ii) whether or not an inflammatory cytokine amount secreted from immune cells can be reduced when the immune cells are brought into contact with the resulting antibody while being stimulated with a TLR7 or TLR9 ligand; (iii) whether or not proliferation of B cells is suppressed when B cells are brought into contact with the resulting antibody while being stimulated with a TLR7 or TLR9 ligand; and (iv) whether or not the disease condition is improved by administering the resulting antibody to an animal model suffering from an inflammatory disease.

The therapeutic agent or preventive containing the anti-TLR7 antibody or anti-TLR9 antibody of the present invention is useful for the treatment of inflammatory diseases. Examples of the inflammatory diseases for which the therapeutic agent or preventive of the present invention is particularly useful include various autoimmune diseases (rheumatoid arthritis (RA), SLE, scleroderma, polymyositis, Sjogren's syndrome, ANCA associated vasculitis, Behcet's disease, Kawasaki disease, mixed cryoglobulinemia, multiple sclerosis, Guillain-Barre syndrome, myasthenia, type 1 diabetes, Graves' disease, Hashimoto's disease, Addison's disease, IPEX, APS type-II, autoimmune cardiomyopathy, interstitial pneumonia, bronchial asthma, autoimmune hepatitis, primary biliary cirrhosis, Crohn's disease, ulcerative colitis, psoriasis, atopic dermatitis, hemolytic anemia, autoimmune thyroiditis, and polyarthritis such as juvenile idiopathic arthritis).

The therapeutic agent or preventive is presumed to be useful for, among these diseases, SLE or psoriasis because TLR7 and/or TLR9 is reported to be involved in the onset mechanism of these diseases.

The therapeutic agent or preventive for inflammatory diseases according to the present invention contains the antibody of the present invention as an effective component and in addition, contains a pharmaceutically acceptable carrier and additive.

Examples of the carrier and additive include, but not limited to, water, saline, pharmaceutically acceptable organic solvents such as phosphate buffer, dextrose, glycerol, and ethanol, collagen, polyvinyl alcohol, polyvinyl pyrrolidone, carboxyvinyl polymer, sodium carboxymethyl cellulose, sodium polyacrylate, sodium alginate, water-soluble dextran, sodium carboxymethyl starch, pectin, methyl cellulose, ethyl cellulose, xanthan gum, gum arabic, casein, agar, polyethylene glycol, diglycerin, glycerin, propylene glycol, vaseline, paraffin, stearyl alcohol, stearic acid, human serum albumin, mannitol, sorbitol, lactose, and a surfactant.

The therapeutic agent or preventive for inflammatory diseases according to the present invention can be provided in various forms, for example, solutions (ex. injections), dispersions, suspensions, tablets, pills, powders, or suppositories. A preferred mode is an injection. It is administered preferably parenterally (for example, intravenously, transdermally, intraperitoneally, or intramuscularly).

The term "therapeutic agent or preventive" as used herein means a medicament causing at least one of recovery and remission of a disease, prevention or retardation of onset, prevention and retardation of the progress of a disease, and relief of at least one of the symptoms associated with a disease.

An administration amount of the medicament composition of the present invention to mammals (for example, humans, mice, rats, guinea pigs, rabbits, dogs, horses, monkeys, and pigs), particularly to humans, differs depending on the symptom, age, sex, weight, and sensitivity difference of a patient, administration route, administration interval, kind of effective component, and kind of formulation and is not particularly limited. For example, from 30 µg to 1000 mg, from 100 µg to 500 mg, or from 100 µg to 100 mg of it can be administered once or in several portions. For administration through injection, from 1 µg/kg to 5000 µg/kg or from 3 µg/kg to 3000 µg/kg of it may be administered once or in several portions based on the weight of a patient.

(Treatment Method)

The present invention embraces a method of treating or preventing autoimmune diseases including a step of administering the antibody of the present invention to a subject.

The disclosure of all the patent documents and non-patent documents cited herein are incorporated herein by reference in its entirety.

EXAMPLES

The present invention will hereinafter be described specifically based on Examples. The present invention is not limited by them. The present invention can be changed into various modes without departing from the principle of the present invention and such a change may be embraced within the range of the present invention.

Example 1: Establishment of Anti-TLR7 Antibody, Detection of Cell Surface TLR7, and TLR7 Response Inhibition Experiment by Anti-TLR7 Antibody

[Material and Method]
Mice and Cells

Wild-type C57BL/6 mice and wild-type Balb/c mice were purchased from Japan SLC, Inc. Unc93B1 D34A Mutant mice (Unc93b1$^{D34A/D34A}$) were offered by Assistant Professor Ryutaro Fukui. TLR7-Deficient mice (TLR7$^{-/-}$) were offered by Dr. Shizuo Akira (Osaka University). Mice were bred in an SPF environment and experiment was performed based on the Code of Ethics of the University of Tokyo.

Ba/F3 Cells, a cell line derived from pro-B cells were cultured using a RPMI culture medium (10% FCS, 50 µM 2ME, penicillin/streptomycin/1-glutamine mixed solution, containing IL-3). Mouse and human TLR3, TLR7, TLR8, and TLR9 having, on the C-terminal side thereof, Flag-His6 added were kindly provided by Associate Professor Ryutaro Fukui (Fukui, R. et al., J Exp Med 2009). PRAT4A-Knocked down M12 cells were kindly provided by Specially appointed Assistant Professor Takuma Shibata (Takahashi, K. et al. J Exp Med 2007).

Reagent and Antibody

Synthesis of CpGB (5'-TCCATGACGTTCCTGATGCT-3') DNA (SEQ ID NO: 35), CpGA (5'-GGGGTCAACGT-TGAGGGGGG-3') DNA (SEQ ID NO: 36), PolyU (5'-UUUUUUUUUUUUUUUUUUUU-3') (SEQ ID NO: 37), and RNA 9.2s-DR (5'-UGUCCUUCAAUGUCCUUCAA-3') (SEQ ID NO: 38) was entrusted to Hokkaido System Science Co., Ltd.

Synthesis of Lipid A was requested to Dr. Koichi Fukase (Osaka University) and it was provided by him.

Pam3CSK4, Poly(I:C), Loxoribine (loxoribine), and Imiquimod (imiquimod) were purchased from Invivogen.

Recombinant mice granulocyte macrophage colony-stimulating factor (GM-CSF) and recombinant mice macrophage colony-stimulating factor (M-CSF), and mouse Flt3 ligand were purchased from PeproTech.

Puromycin and neomycin were purchased from Sigma. A RPMI culture medium and a DMEM culture medium were purchased from GIBCO. As a recombinant mouse IL-3, that prepared using CHO cells in the present laboratory was used.

Determination of Amino Acid Cleavage Site of TLR7

It is reported that TLR7 is cleaved (Ewald et al. Nature 2008). In order to determine the amino acid cleavage site of TLR7, therefore, N-terminal amino acid sequence analysis was performed by the Edman degradation method. A preparation process of a sample is shown below.

As cells used for N-terminal amino acid sequence analysis, RAW264.7 cells obtained by forced expression of TLR7 (TLR7-GFP) having, on the C terminal side thereof, Green Fluorescent Protein (GFP) added were used and they were increased to $1 \times 10^{10}$ and collected.

The cells thus collected were lysed in an ice-cooled lysis buffer (having the composition as shown in Table 1) for 30 minutes and a lysate was collected after centrifugation. The lysate thus collected was added to anti-GFP antibody (FM264) beads and the resulting mixture was stirred at 4° C. for 12 hours to cause immunoprecipitation. The immunoprecipitated beads were collected and washed four times with Washing buffer (0.1% Triton X-100, 30 mM Tris/HCl pH 7.4, 150 mM NaCl). With Elution buffer (0.1% Triton X-100, 30 mM Glycine/HCl pH 2.5, 150 mM NaCl), TLR7-GFP was eluted. The protein thus eluted was subjected to polyacrylamide electrophoresis and TLR7-GFP was confirmed by Coomassie Brilliant Blue staining. After confirmation of the eluted protein, a solution containing the TLR7-GFP was dialyzed with a dialysis buffer (0.1% Triton X-100, 10 mM NaCl). After collection, the dialysate solution was lyophilized for 4.5 hours. The protein thus lyophilized was lysed in a 50 µl Sample buffer (62.5 mM Tris/HCl pH 6.8, 10% Glycerol, 2% sodium dodecyl sulfate (SDS), 0.025% bromophenol blue, 5% 2-mercaptoethanol), subjected to polyacrylamide electrophoresis, and transcribed into a PVDF membrane in a CAPS transfer buffer (1×CAPS pH 11.0, 10% methanol). The TLR7 thus transcribed was visualized by Coomassie Brilliant Blue staining and the TLR7 C-terminal protein band thus cleaved was excised.

After the PVDF membrane thus excised was washed twice with a CAPS buffer, APRO was asked to analyze the resulting sample for the N-terminal amino acid sequence determination by the Edman degradation method.

Preparation of Anti-TLR7 Monoclonal Antibody

The anti-mouse TLR7 antibody A94B10 was prepared as follows.

As an immunized animal, Balb/c background TLR7-deficient mice obtained by back-crossing C57BL/6 background TLR7-deficient mice to Balb/c mice six times were used. As an antigen, Ba/F3 cells transfected with Flag-His6 epitope-added mouse TLR7 (mTLR7-fH) were used.

Immunization was performed by intraperitoneally administering an immunogen to the mice. The mice were administered with an antigen mixed with CFA on day 1 of immunization, with the antigen mixed with IFA on day 8 of immunization, and with the antigen diluted with 1×PBS three times every week. On day 5 after final immunization day, the spleen was excised and the spleen cells thus obtained were fused with Sp2/o cells derived from mouse myeloma. The monoclonal antibody available from the resulting hybridoma may hereinafter be called "A94B10 antibody".

In order to select a clone of a hybridoma that produces an antibody specifically recognizing mouse TLR7 in a supernatant, intracellular staining of Ba/F3 cells in which mTLR7-fH, an antigen, had been forcibly expressed was performed using a 0.1% saponin-containing FACS solution (1×PBS, 2.5% FBS, 0.1% NaN$_3$), followed by selection with flow cytometry. From the hybridoma cells thus obtained, a monoclonal antibody-producing hybridoma line A94B10 producing an anti-mouse TLR7 antibody was established.

The isotype of the clone A94B10 thus obtained was found to be IgG1. Detection of the anti-mouse TLR7 antibody was achieved by detecting endogenous TLR7 that had been expressed in BM-MCs, BM-cDCs, BM-pDCs, and B cells derived from the spleen cells by flow cytometry, immunoprecipitation, and a confocal microscopy. The above facts suggest that the hybridoma line thus established produces a mouse TLR7-specific antibody.

Induction of BM-MCs, BM-cDCs, and BM-pDCs

After hemolysis treatment of bone marrow cells collected from the femur and tibia of mice, BM-MCs, BM-cDCs, and BM-pDCs were induced. BM-MCs were induced by seeding the bone marrow cells at a $5 \times 10^6$ per 10-cm diameter bacteria-culture Petri dish (greiner Bio-one) and culturing them for 7 days in a DMEM culture medium containing 100 ng/ml of recombinant murine M-CSF (PeproTech). BM-cDCs was induced by seeding the bone marrow cells at $1 \times 10^7$ per 10-cm diameter cell culturing Petri dish (greiner Bio-one) and culturing them for 7 days in a RPMI culture medium containing 10 ng/ml of mouse GM-CSF (peprotech) (Kaisho, T. et al., J Immunol 2001). In inducing BM-cDCs, half of the culture medium was replaced with a new GM-CSF-containing RPMI culture medium every two days and an amount of the culture medium was increased with cell proliferation.

The BM-pDCs was induced by seeding the bone marrow cells at $1 \times 10^7$ per 10-cm diameter cell culturing Petri dish and culturing them for 7 days in a RPMI culture medium containing 30 ng/ml of mouse Flt3 ligand (peprotech). In inducing the BM-pDCs, half of the culture medium used for induction was replaced with a new Flt3 ligand-containing RPMI culture medium every day during the induction period and an amount of the culture medium was increased with cell proliferation. The BM-pDCs is known to be a CD11c-positive B220 positive cell group as a cell surface marker.

Then, the BM-pDC thus induced was stained with anti-mouse CD11c-PE and anit-mouse B220-APC and CD11c-positive B220-positive cells were isolated by FACS Aria (BD).

Purification of B Lymphocytes

CD43 is not expressed in resting or normal peripheral B cells. Spleen B cells were purified by making use of this fact and collecting a CD43-negative spleen cell fraction (Nagai, Y. et al., J Immunol 2005). The spleen was excised from wild-type mice and cells were isolated from the spleen tissue by using a slide glass. After hemolysis treatment, CD43 MicroBeads (Miltenyi Biotec K.K.) were added to the spleen cells and the resulting mixture was mixed at 4° C. for 30 minutes. After washing twice with Running buffer (1×PBS, 2% FBS, 2 mM EDTA), a CD43 negative cell group was isolated using the deplete program of AutoMACS. An isolation efficiency of the B cells was confirmed by flow cytometry using FACS Callibur (BD). The B cells thus isolated were cultured in a 10% FBS-added RMPI culture medium.

Thymidine Incorporation Assay

The cell proliferation activity was quantitatively determined by measuring an incorporation amount of [3H] thymidine in cells. The B cells obtained by purification of spleen cells were seeded in a 96-well flat-bottom plate at $1 \times 10^5$/well and stimulated with a plurality of kinds of TLR ligands. After stimulation for 72 hours, they were cultured for further 5 hours in the presence of 1 μCi/ml of [3H] thymidine and an amount of [3H]thymidine incorporated in the cells was measured using a cell harvester system (Inotech) (Nagai et al. J Immunol 2005).

Enzyme-Linked Immunosorbent Assay (ELISA)

A plurality of kinds of TLR ligands were added to cells plated at $1 \times 10^5$/well in a 96-well flat-bottom plate. The supernatant after 24 hours was provided for sandwich ELISA and the concentration of each of TNFα, IL-6, IL-12p40, and RANTES was measured using ELISA Kit (R&D Systems) and the concentration of IFN-α was measured using ELISA Kit (PBL Interferon Source).

Flow Cytometry

Flow cytometry analysis was performed using FACS Callibur (BD). Cells to be analyzed was washed with a FACS solution and then provided for staining. The following were antibodies used for the analysis. Fluorescein (FITC)-conjugated anti-mouse CD4 (L3T4), Phycoerythrin (PE)-conjugated anti-mouse CD62L (MEL-14), Allophycocyanin (APC)-conjugated anti-mouse CD8a (53-6.7), APC-conjugated anti-mouse Ly6G (1A8), PEcy7-conjugated anti-mouse CD19 (1 D3), and Streptavidin-APC were purchased from BD pharmingen. Biotin conjugated anti-mouse ICOS (7E.17G9), Biotin mouse IgG1, κ Isotype ctrl antibody (MOPC-21), FITC-conjugated anti-mouse B220 (RA3-6B2), FITC-conjugated anti-mouse CD11b (M1/70), FITC-conjugated anti-mouse CD71 (R17217), PE-conjugated anti-mouse Ter119 (TER119), PerCP/Cy5.5-conjugated anti-mouse CD11c (N418), APC-conjugated anti-mouse/ human CD44 (IM7), APC-conjugated anti-mouse B220 (RA3-6B2), and Alexa488-conjugated anti-mouse GL-7 (GL-7) were purchased from eBioscience. PE-Conjugated anti-mouse CD11c (N418), PerCP/Cy5.5-conjugated anti-mouse Ly6C (HK1.4), PerCP-conjugated anti-mouse CD4 (GK1.5), APC-conjugated anti-mouse IgD (11-26c, 2a), Pacific Blue-conjugated anti-mouse PDCA-1(927), and Streptavidin-PE were purchased from Biolegend. R-PE Conjugated goat anti-mouse IgG (H+L) (Absorbed against human immunoglobulins) and APC-conjugated anti-mouse Lamp1 (1 D4B) were purchased from Southern Biotech.

Biotin-conjugated anti-mouse Flag (M2) was purchased from Sigma Aldrich. As Biotin-conjugated anti-mouse TLR4/MD2 (MTS510), that prepared in the present laboratory was used (Akashi, S. et al., J Immunol 2000).

Preparation of Retrovirus Vector and Knockdown Vector and Transfection into Cells Human TLR7 added, on the C terminal side thereof, with Flag-His6 was incorporated in a retrovirus vector pMXs carrying no drug resistance gene.

In order to determine the epitope of the anti-TLR7 monoclonal antibody, an N terminal region TLR7 (from 27-th phenylalanine to 457-th proline) and a C terminal region TLR7 (from 461-st glutamic acid to 837-th aspartic acid) were prepared with the amino acid cleavage site of TLR7 as a boundary. They were incorporated in a pDisplay vector (Invitorgen) using InFusion enzyme (TaKaRa) and incorporated further in a retrovirus vector pMXp that had already carried a puromycin-resistant gene. The vector enables an intended protein expressed by the incorporated gene to appear in the cell surface and add a HA antigen to its N-terminal.

For incorporation of the retrovirus vector in retrovirus particles, Plat-E cells, a packaging cell line derived from HEK293, was transfected using FuGene6 (Roche). Twenty four hours after transfection, the supernatant was collected and it was secured as a virus suspension. The resulting virus suspension was mixed with DOTAP (Roche). The resulting mixture was added to cells to be transfected, followed by centrifugation for one hour at 2000 rpm.

After transfection, 2 µg/ml of puromycin was added to the cells transfected with pMXp and 4 µg/ml of neomycin was added to the cells transfected with pSSCN to select transfected cells.

pMX and retroviral vectors (pMX, pMXp) derived therefrom and necessary for retrovirus preparation, and Plat-E, a packaging cell line, were kindly given by Prof. Toshio Kitamura, Institute of Medical Science/the University of Tokyo.

Immunoprecipitation and Western Blotting

Protein expression of TLR7 was analyzed using western blotting. After washing twice with 1×PBS, the cells were collected. For detection of protein expression, the cells thus collected were lysed using an ice-cold lysis buffer (1% Digitonin, 20 mM Tris-HCl (pH 7.4), 150 mM NaCl, 1 mM $CaCl_2$, 1 mM $MgCl_2$, 10% Glycerol, 1 mM DTT, and Complete protease Inhibitor Cocktail (Roche)) for 30 minutes and the lysate after centrifugation was collected. The lysate thus collected was added to N-hydroxysuccinimide-activated Sepharose 4FF beads bound to the anti-TLR7 monoclonal antibody (A94B10) and the resulting mixture was stirred at 4° C. for 2 hours. By the above procedure, TLR7 that had expressed in the cells was immunoprecipitated. After stirring, the beads were washed three times with an ice-cooled washing buffer (0.1% Digitonin, 20 mM Tris/HCl (pH 7.4), 150 mM NaCl, 1 mM $CaCl_2$, 1 mM $MgCl_2$, 0.1% Glycerol, and 1 mM DTT). To the beads thus washed was added an SDS sample buffer (125 mM Tris/HCl [pH 6.8], 20% glycerol, 4% SDS, 10% 2-ME, and 0.005% bromophenol blue) and the resulting mixture was subjected to protein denaturation treatment by heating at 96° C. for 5 minutes. The samples thus prepared were subjected to polyacrylamide electrophoresis and protein was transferred to a PVDF membrane, followed by western blotting.

The following are antibodies used for western blotting. Rabbit anti-mouse Grb2 (C-23) was purchased from Santa Cruz Biotechnology. An anti-mouse TLR7 polyclonal antibody (TLR7N) was purchased from eBioscience.

Biotinylation of the cell surface and immunoprecipitation and western blotting subsequent thereto were performed by the following process.

The surface of the cells washed twice with HBSS (−) was biotinylated using 0.1 mg/$5 \times 10^7$ cells of a biotinylating reagent prepared by adjusting EZ-Link Sulfo-NHS-LC-Biotin (Thermo scientific) with a Biotin labeling buffer (1×PBS, 15 mM HEPES, 150 mM NaCl) to 10 mg/ml. The biotinylated cells were washed three times with HBSS(−) and collected. The cells thus collected were lysed for 30 minutes with an ice-cold lysis buffer and the lysate after centrifugation was collected. The lysate thus obtained was added to N-hydroxysuccinimide-activated Sepharose 4FF beads bound to the anti-TLR7 monoclonal antibody (A94B10). The resulting mixture was stirred at 4° C. for 12 hours. By the above procedure, endogenous TLR7 was immunoprecipitated. After stirring, the beads were washed three times with an ice-cooled washing buffer. The beads thus washed were adjusted with an SDS sample buffer. The samples thus adjusted were subjected to polyacrylamide electrophoresis. The protein was transferred to a PVDF membrane, followed by western blotting.

The antibody used for western blotting after biotynylation of the cell surface was detected with streptavidin-labeled horseradish peroxidase (StAv-HRP). The anti-mouse TLR7 polyclonal antibody (TLR7N) was purchased from eBioscience.

Statistical Processing

In an experiment of administering an antibody to mice, a significant difference test of data between an anti-TLR7 monoclonal antibody administration group and a control antibody administration group was performed according to Student's t-test. Risk factors less than 0.01 in T test were judged that the difference between the compared groups was significant.

TLR7 Response Inhibition Experiment with Anti-TLR7 Monoclonal Antibody (In Vitro Test)

As cells, BM-MCs, BM-cDCs, BM-pDCs, and B cells isolated from spleen cells were used. A 96-well flat-bottom plate was seeded with $1 \times 10^5$ of each of BM-MCs, BM-cDCs, and BM-pDCs and the anti-TLR7 antibody was added at respective concentrations. Four hours after addition of the antibody, a TLR ligand was added to the seeded and cultured cells. Twenty four hours after addition of the TLR ligand, the supernatant was collected. The supernatant thus collected was subjected to ELISA to measure an amount of cytokine produced by the stimulation with the ligand.

(In Vivo Test)

It is reported that Unc93B1 D34A mutant mice developed thrombocytopenia and splenomegaly as a result of excessive TLR7 response (Fukui et al. immunity 2011). Administration of the antibody was started during the term from 12 weeks of age to 16 weeks of age of the Unc93B1 D34A mutant mice who were recognized to show a decrease in the number of blood platelets (85.3 [$10^4$/µl] in wild-type mice, while 32.4 [$10^4$/µl] in the Unc93B1 D34A mutant mice). The antibody was administered through intravenous injection and its amount was 200 µg/mouse. The antibodies used were A94B10 antibody and a control antibody and they were administered every week. To precisely determine the influence on the antibody administration to a decrease in the number of blood platelets, the blood was taken from the tail every two weeks after administration of the antibody and the number of blood platelets was counted by a hemocytometer ("Celltac α MEK-6450"; NIHON KOHDEN). Ten weeks after administration of the antibody, the spleen was excised from the D34A mutant mice and it was weighed. Further, the spleen and lymph nodes (upper arm, axillary, groin lymph nodes) excised from the mice were analyzed for cell population by flow cytometry.

Amino Acid Sequence Analysis of Antibody and CDR

Total RNA was isolated from hybridoma lines A94B10, B33A4, and C34A1 and purified using RNeasy Mini Kit purchased from QIAGEN. After heavy chain isotype and light chain-specific 1st strand cDNA synthesis from the total RNA was performed using a SMARTer RACE cDNA Amplification Kit purchased from Clontech, 5'-RACE PCR was carried out to synthesize full-length heavy chain and light chain cDNAs including a variable region. The resulting cDNAs were inserted into a pMD20-T vector by using a Mighty TA-cloning Kit purchased from TaKaRa. Then, the base sequence analysis was entrusted to FASMAC and the amino acid sequence was determined from the resulting base sequence. The CDR sequence was determined by comparing the amino acid sequence using a database AHo's Amazing Atlas of Antibody Anatomy provided by the University of Zurich.

[Results]

Establishment of Anti-TLR7 Monoclonal Antibody and Detection of Cell Surface TLR7

An A94B10 antibody, a monoclonal antibody against mouse TLR7, was established in order to study the intracellular localization of endogenous TLR7 of primary immune cells. It has been believed that TLR7 is present only in intracellular vesicles, but the anti-TLR7 monoclonal antibody has elucidated the presence of TLR7 in the cell surface of bone marrow-derived macrophages (FIG. 1A).

Figure 1B:
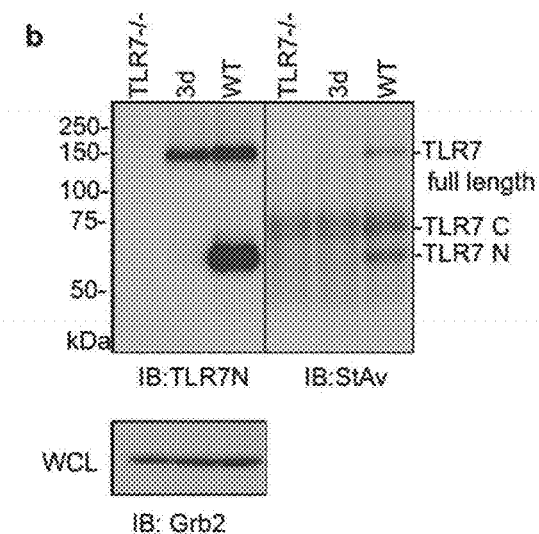
FIG. 1B, the cell surface of BM-MCs of each of the wild-type, Unc93b1$^{3d/3d}$, and TLR7$^{-/-}$ was biotinylated; immunoprecipitation was performed with an anti-TLR7 antibody; and cell surface TLR7 (right) was detected using streptavidin and endogenous TLR7 (left) was detected using an anti-TLR7 antibody. The term "TLR7 full length" means full length TLR7, the term "TLR7C" means a TLR7 fragment on the C-terminal side after processing, and the term "TLR7N" means a TLR7 fragment on the N terminal side after processing.

Specificity of staining was confirmed by the fact that the macrophages derived from the bone marrow of TLR7-knockout mice were not stained. Further, in order to confirm the expression of TLR7 in the cell surface, the cell surface was biotinylated and TLR7 was immunoprecipitated from the bone marrow-derived macrophages. The TLR7 thus precipitated was detected by streptavidin or the anti-TLR7 antibody. TLR7 was proteolytically cleaved by endo-lysosome. The full-length TLR7 and the cleaved TLR7 were detected in wild type cells by streptavidin, but they were not detected in the TLR7 knockout cells (FIG. 1B). This shows that both the processed TLR7 and unprocessed TLR7 are expressed in the cell surface. The full-length and cleaved TLR7s are presumed to be derived from the Golgi apparatus or endo-lysosome, respectively.

The cell surface TLR7 was hardly detected in the bone marrow-derived classical or plasma cell-like dendritic cells (FIG. 1A), but it was detected from the spleen-derived resident pDC or cDC. The reason for difference between the cell surface TLR7 in vitro differentiated DC and that in vivo resident DC is unknown. The CD11b+ macrophage/monocyte and neutrophil in the spleen also expressed the cell surface TLR7, but the number of it was much smaller than that of the spleen-derived DC (data are not shown). The B cells also responded to the TLR7 ligand but the cell surface TLR7 was not detected (data are not shown).

Figure 1C:
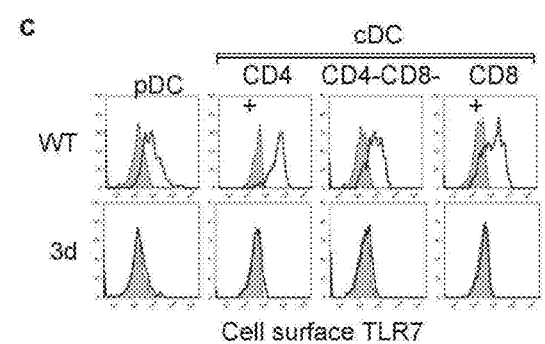
FIG. 1C shows the results of measuring the cell surface TLR7 in each subset of the spleen-derived DC by means of flow cytometry. White histograms show the cell surface staining with an anti-TLR7 antibody performed for spleen-derived DC of CD4$^+$, CD4$^-$CD8$^-$, and CD8$^+$. DC was prepared using a wild-type or Unc93b1$^{3d/3d}$ mouse.

Transport of TLRs 7 and 9 from the endoplasmic reticulum (ER) to the endo lysosome requires two ER resident proteins PRAT4A and Unc93B1. Cell surface TLR7 was not detected in the spleen DC derived from Unc93B1$^{3d/3d}$ mice (FIG. 1C), Unc93B1-function deficient mice, or from PRAT4A$^{-/-}$ mice (data are not shown). This suggests that both PRAT4A and Unc93B1 are necessary for the transport of TLR7 to the cell surface. The cell surface TLR7 was detected (data are not shown) in the spleen MyD88$^{-/-}$ cDC. This suggests that the TLR signal is not required for the expression of TLR7 in the cell surface. Expression of TLR7 in B cells is known to be kept by type I interferon. In IFNAR$^{-/-}$ cDC, however, no change in the expression of TLR7 in the cell surface was found. The type I interferon is not required for the expression of TLR7 in the cell surface.

Studying of a cleavage site of TLR7 has revealed that it is cleaved between the 460-th leucine and 461-st glutamic acid, and 461-st glutamic acid and 462-nd alanine (FIG. 9A). It has been found that the A94B10 antibody binds to the N terminal region TLR7 (TLR7N; from 27-th phenylalanine to 457-th proline) and does not bind to the C terminal region TLR7 (TLR7C; from 461-st glutamic acid to 837-th aspartic acid) (FIG. 9B).

TLR7 Response Inhibition Experiment by Anti-TLR7 Monoclonal Antibody (1)

TLR7 has been thought to recognize RNA at endolysosome (Ewald, S. E. et al. J Exp Med 2011). An anti-TLR7 monoclonal antibody was added to various immune cells in order to study the role of the cell surface TLR7 in the RNA recognition.

Figure 2:
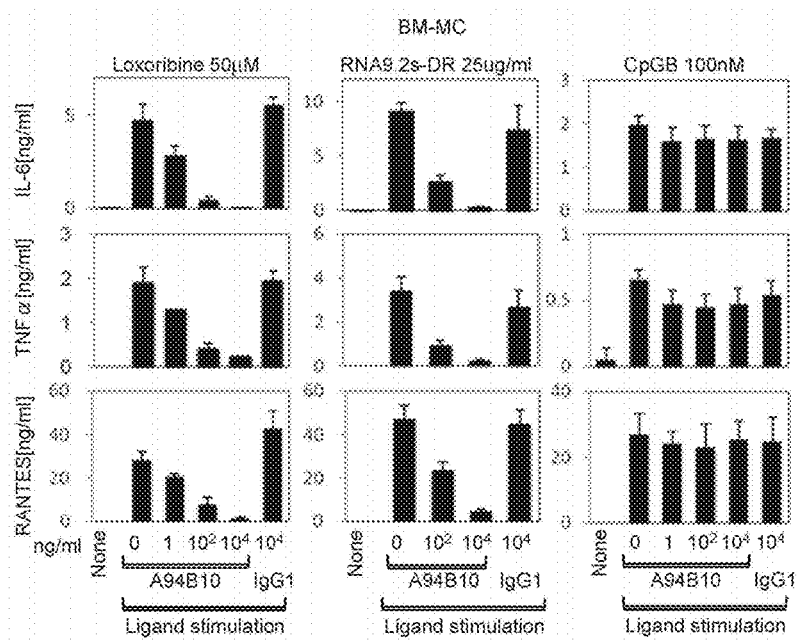
FIG. 2 shows the results of stimulating BM-MCs with loxoribine or RNA9.2 which is a TLR7 ligand, or CpG-B which is a TLR9 ligand and measuring production of IL-6, TNFα, and RANTES by means of ELISA. With regard to the results, the results of the triplicate measurements are shown as mean value and standard deviation.
Figure 3:
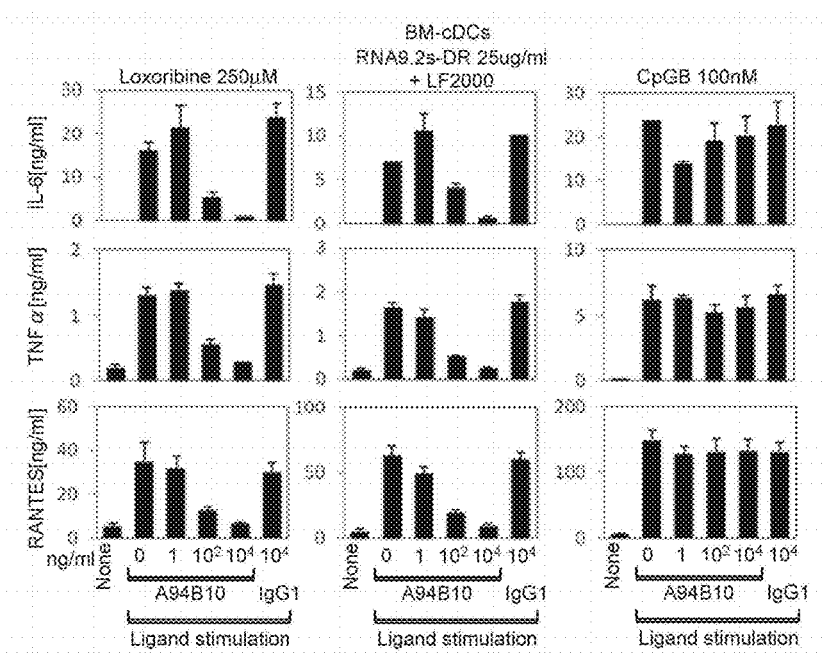
FIG. 3 shows the results of stimulating BM-cDCs with loxoribine or RNA9.2 which is a TLR7 ligand, or CpG-B which is a TLR9 ligand and measuring production of IL-6, TNFα, and RANTES by means of ELISA. With regard to the results, the results of the triplicate measurements are shown as mean value and standard deviation.
Figure 4:
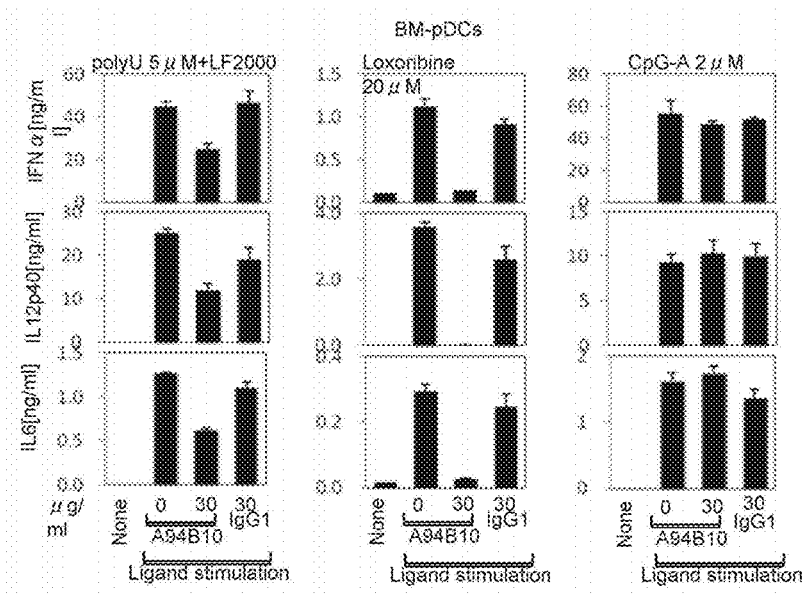
FIG. 4 shows the results of stimulating BM-pDCs with loxoribine or polyU which is a TLR7 ligand, or CpG-A which is a TLR9 ligand and measuring production of IFNα, IL-12 p40, and IL-6 by means of ELISA. With regard to the results, the results of the triplicate measurements are shown by the mean value and standard deviation.
Figure 5:
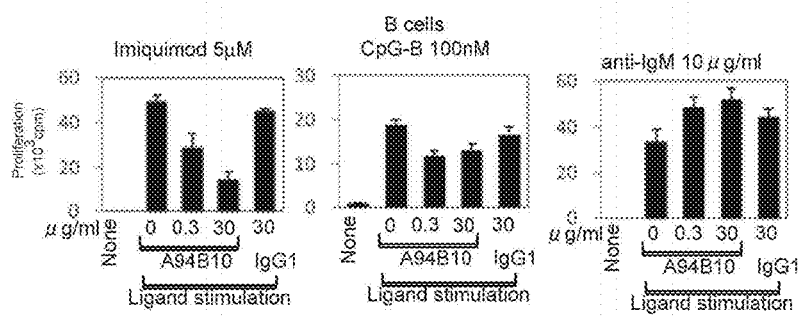
FIG. 5 shows the results of stimulating spleen-derived B cells with Imiquimod which is a TLR7 ligand, CpG-B which is a TLR9 ligand, or an anti-IgM antibody and measuring proliferation of B cells in terms of thymidine incorporation. With regard to the results, the results of the triplicate measurements are shown by the mean value and standard deviation.

Contrary to expectations, the anti-TLR7 monoclonal antibody concentration-dependently inhibited the production of IL-6, TNF-α, IL-12, and RANTES (CCL5) by loxoribine, a low molecular TLR7 ligand, or bone marrow-derived macrophages stimulated with synthetic RNA (FIG. 2A). TLR9-dependent cytokine production by CpG-B, a TLR9 ligand, showed no change. Contrary to expectations, TLR7 specific inhibition was observed also in BM-cDCs and BM-pDCs (shown in FIGS. 2 and 3, respectively) in which almost no cell surface TLR7 was detected. A BM-pDCs reaction to polyuridylic acid (Poly U) was significantly inhibited, though the inhibition level was a moderate level (FIG. 4). Proliferation of B cells responsive to imiquimod, a low molecular TLR ligand, was also inhibited significantly (FIG. 5). The above results have shown that the anti-TLR7 monoclonal antibody can inhibit TLR7 response of BM-cDCs, BM-pDCs, BM-MCs, and spleen-derived B cells.

TLR7 Response Inhibition Experiment by Anti-TLR7 Monoclonal Antibody (2)

Next, the inhibitory effect of the anti-TLR7 monoclonal antibody was studied using mice suffering from a TLR7-dependent inflammatory disease. Unc93b1$^{D34A/D34A}$ mice in which the 34-th aspartic acid of Unc93b1 gene has been substituted with alanine has systemic lethal inflammation due to hyperreaction of TLR7 (Fukui et al. immunity 2011).

Figure 6A:
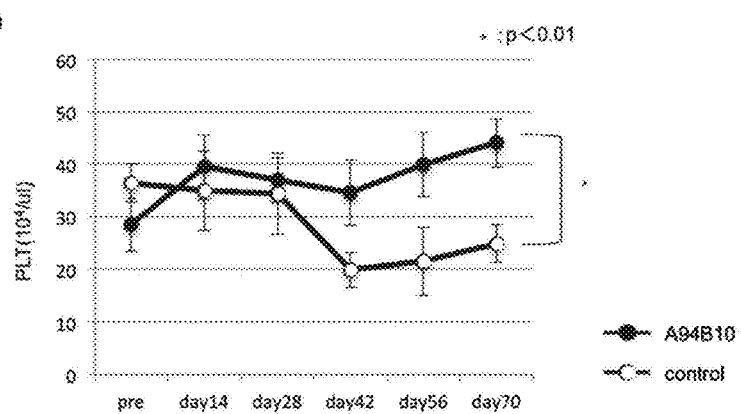
FIG. 6A shows the results of administering a Unc93b1$^{3d/3d}$ mouse with 200 μg of an anti-TLR7 antibody or a control antibody once a week and measuring the platelet level in peripheral blood every other week. The platelet levels shown in the graph are those before and after administration of the antibody 10 times. Each group consists of 7 mice. *:P<0.01

The systemic inflammation causes thrombocytopenia that can be monitored easily from the peripheral blood. A monoclonal antibody was administered by injection to Unc93b1$^{D34A/D34A}$ mice three to four months of age that had already suffered thrombocytopenia, in order to study the therapeutic effect of the anti-TLR7 antibody. The monoclonal antibody (200 μg/per mouse) was injected once a week and the number of blood platelets in the peripheral blood was counted every other week. After 10-times treatment, the number of the blood platelets of the mice in the anti-TLR7 monoclonal antibody administration group increased, while it showed a gradual decrease in the control antibody administration group (FIG. 6A).

Figure 6B:
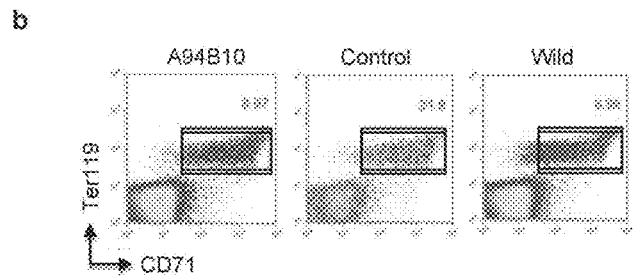
FIG. 6B shows the results of treating mice with an anti-TLR7 antibody or a control antibody for 10 weeks, sacrificing them, and analyzing a ratio of splenic erythroblasts through flow cytometry.
Figure 6C:
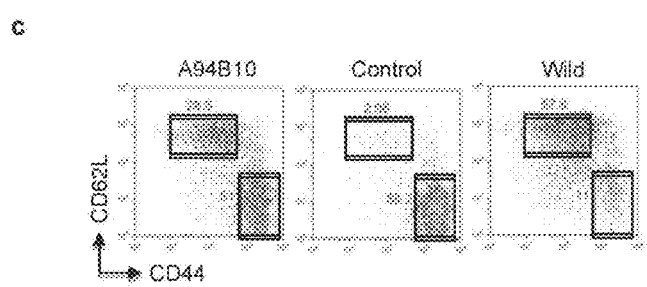
FIG. 6C shows the results of treating mice with an anti-TLR7 antibody or a control antibody for 10 weeks, sacrificing them, and analyzing a ratio of CD4$^+$ memory T cells through flow cytometry.
Figure 6D:
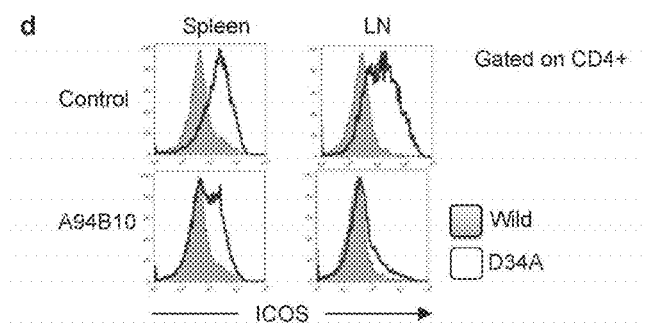
FIG. 6D shows the results of treating mice with an anti-TLR7 antibody or a control antibody for 10 weeks, sacrificing them, and analyzing expression of ICOS of CD4$^+$ T cells through flow cytometry.

After treatment with the anti-TLR7 monoclonal antibody for 10 weeks, the mice were sacrificed and the disease condition was analyzed. In the Unc93b1$^{D34A/D34A}$ mice, the number of erythroblasts in the bone marrow cells of the spleen increased. A proportion of the erythroblasts in the spleen was markedly lower in the anti-TLR7 antibody administration group than in the control antibody administration group (FIG. 6B). T cells were activated and differentiated into memory T cells with enhancement of the expression of a costimulatory molecule ICOS in the cell surface. A proportion of the expression of the memory T cells and ICOS on the CD4+ cells in the Unc93b1$^{D344/D344}$ mice were markedly smaller than that in the group treated with the control antibody, respectively (FIGS. 6C and 6D). The above results show that the anti-TLR7 antibody improves TLR7-dependent systemic inflammation of Unc93b1$^{D344/D344}$ mice.

TLR7 Response Inhibition Experiment by Anti-TLR7 Monoclonal Antibody (2)

Next, whether or not the anti-TLR7 monoclonal antibody suppressed cytokine production induced in vivo by a TLR7 ligand was studied. According to the schedule shown on the upper side of FIG. 10, the A94B10 antibody and R848, a TLR7 ligand, were administered and the concentrations of IL-6 and IFNα in the blood were measured.

The results are shown on the lower side of FIG. 10. It has been confirmed that the A94B10 antibody significantly suppressed, in a concentration dependent manner, cytokine production induced by R848 administration.

TLR7 Response Inhibition Experiment by Anti-TLR7 Monoclonal Antibody (3)

Next, it was studied whether or not the anti-TLR7 monoclonal antibody suppressed skin inflammation induced by a TLR7 ligand in vivo. The degree of inflammation was evaluated by administering the A94B10 antibody according to the schedule shown in the upper side of FIG. 11 and intradermally administering Imiquimod, a TLR7 ligand, to the ear of the mouse (Intradermal; i.d.), and measuring the thickness of the ear.

The results are shown in FIG. 11. It has been confirmed that the A94B10 antibody significantly suppressed skin inflammation induced by Imiquimod.

TLR7 Response Inhibition Experiment by Anti-TLR7 Monoclonal Antibody (4)

Next, it was studied whether or not the anti-TLR7 monoclonal antibody suppressed inflammation in a psoriasis mouse model. The psoriasis model was prepared by administering IL-23 to the ear of mice according to the schedule shown on the upper side of FIG. 12 and the A94B10 antibody was administered thereto. It is known that mice administered with IL-23 have enhanced TLR7 expression (left bottom of FIG. 12) and become a model having psoriasis very similar to that of human psoriasis. The degree of inflammation was evaluated by measuring the thickness of the ear.

The results are shown in the right bottom of FIG. 12. It has been confirmed that the A94B10 antibody significantly suppressed the inflammation of the psoriasis mouse model induced by IL-23.

Amino Acid Sequence Analysis of Antibody, CDR, and Epitope

The heavy-chain amino acid sequence and the light-chain amino acid sequence, each of the monoclonal antibody available from a hybridoma line A94B10 are represented by SEQ ID NO: 9 and SEQ ID NO: 10, respectively. The amino acid sequence of the heavy chains CDR 1 to 3 and that of the light chains CDR 1 to 3, each of the above antibody, are represented by SEQ ID NOs: 3 to 5 and SEQ ID NOs: 6 to 8, respectively.

A94B10 Epitope Analysis

Fragments of amino acids of TLR7 represented by SEQ ID NO: 1 from position 27 to position 457, from position 27 to position 364, from position 27 to position 312, and from position 27 to position 226 were cause to express in a cell line and binding between each of the fragments and the A94B10 antibody was measured by flow cytometry in order to determine the epitope of the A94B10 antibody as shown on the upper side of FIG. 13.

The results are shown on the bottom side of FIG. 13. The A94B10 antibody did not bind to TLR7N$_{27-312}$ but bound to TLR7N$_{27-364}$, suggesting that the A94B10 antibody had an epitope in the vicinity of a region of the amino acid sequence of TLR7 from position 313 to position 364.

As another experiment for determining the epitope of the A94B10 antibody, various chimeric TLR7s composed of mouse TLR7 and human TLR7 were prepared as shown on the upper side of FIG. 14 and binding between each of the chimeric TLR7s and the A94B10 antibody was measured using a flow cytometry.

mTLR7$_{1-227}$, mTLR7$_{1-275}$, and mTLR7$_{1-313}$ have the sequence of mouse TLR7 at from position 1 to position 227, from position 1 to position 275, from position 1 to position 313 from the N terminal, respectively, and have the sequence of human TLR7 on the C terminal side. Each of mTLR7$_{228-313}$, mTLR7$_{228-275}$, and mTLR7$_{275-313}$ has the human TLR7 at the N terminal and C terminal and has the mouse TLR7 at the center.

The results are shown on the lower side of FIG. 14. The A94B10 antibody did not bind to the chimeric TLR7 containing the mouse TLR7$_{1-274}$ but it bound to the chimeric TLR7 containing the mouse TLR7$_{1-313}$ and the mouse TLR7$_{275-313}$, suggesting that the A94B10 antibody had an epitope in the vicinity of a region of the amino acid sequence of TLR7 from position 275 to position 313.

Example 2: Establishment of Anti-TLR9 Antibody and Detection of Cell Surface TLR9

[Material and Method]

Establishment of Anti-Mouse TLR9 Monoclonal Antibody

In order to establish a monoclonal antibody (mAb) against mouse TLR9, BALB/c TLR9$^{-/-}$ mice were immunized with Ba/F3 cells(Ba/F3_mTLR9) that expressed mouse TLR9. Four days after final immunization, the spleen cells were fused with the SP2/0 myeloma cells. Hybridomas producing anti-mouse TLR9 mAb were selected by flow cytometry based on the staining of the Ba/F3 cells used for immunization. Three monoclonal antibodies J15A7 (IgG1/κ), C34A1 (IgG2a/κ), and B33A4 (IgG2a/κ) were established.

Cell Staining

For staining BM cells and spleen cells, they were pre-incubated with an anti-CD16/CD32 antibody (clone: 93), stained with an antibody specific to the following markers labeled with a fluorescent substance, and subjected to flow cytometry: CD4 (GK1.5), CD8a (53-6.7), CD11c (HL3), B220 (RA3-6B2), and PDCA-1 (927, 129c1).

A suspension of only spleen cells was prepared according to the method of Shibata, et al. (Shibata, T., et al. Int Immunol 2012). The cells and biotinylated mAb were incubated at 4° C., diluted with a staining buffer (1×PBS, 2.5% FBS and 0.1% NaN$_3$), and then incubated with streptavidin-bound antibody. For intracellular staining, the cells were permeabilized with 0.05% or 0.1% saponin ((Sigma-Aidrich (S5421) or WAKO (193-00162)) in a staining buffer and a step subsequent thereto was also performed in a saponin buffer. The cells thus stained were analyzed by FACSCalibur or FACSAri flow cytometer (BD Biosciences).

Immunoprecipitation and Western Blotting

The cells were washed with and lysed in a lysis buffer (1% Digitonin, 20 mM Tris-HCl (pH 7.4), 150 mM NaCl, 1 mM CaCl$_2$, 1 mM MgCl$_2$, 10% Glycerol, 1 mM DTT and Complete protease Inhibitor Cocktail (Roche)). After incubation on ice, the lysate was centrifuged to remove impurities. For immunoprecipitation, anti-mouse TLR9mAb-bound Sepharose 4FF beads activated with an anti-HA matrix (Roche clone: 3F10) or N-hydroxysuccinimide were added to the cell lysate and the resulting mixture was incubated at 4° C. The beads were washed three times with 0.1% digitonin and the protein thus bound thereto was eluted in a boiled SDS sample buffer (125 mM Tris/HCl [pH 6.8], 20% glycerol, 4% SDS, 10% 2-ME, 0.005% bromophenol blue). After electrophoresis, the sample was transferred to a PVDF membrane and provided for immunoblotting.

Figure 7A:
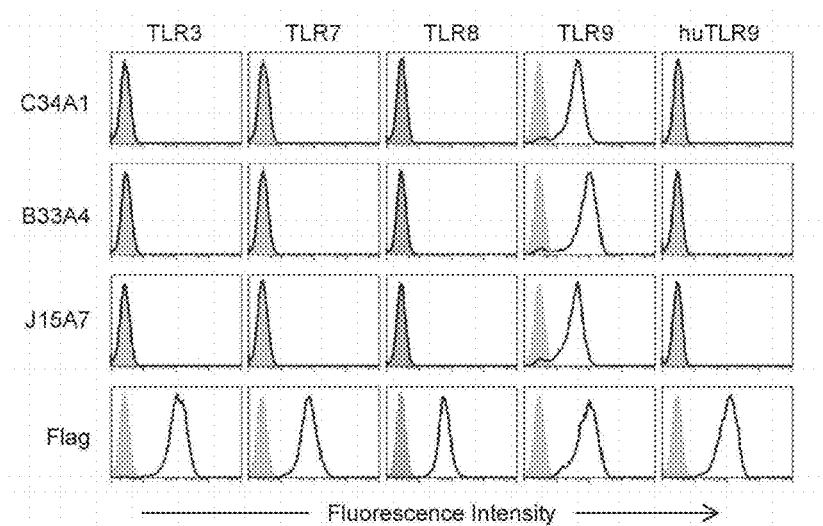
FIG. 7A shows the results of subjecting Ba/F3 cells expressing mouse TLR3, 7, 8 or 9, or human TLR9 to membrane permeability staining with the anti-TLR9 antibody or anti-flag antibody shown in this drawing. TLR9 was labeled, at the C terminal thereof, with a flag epitope.

[Results]
Establishment of Anti-TLR9 Monoclonal Antibody Specific to TLR9N or TLR9C Three monoclonal antibodies against TLR9 were established for studying endogenous TLR9. Specificity of the monoclonal antibodies was confirmed by membrane permeability staining of Ba/F3 cells that expressed TLR3, 7, 8, and 9. The anti-mouse TLR9 antibody specifically reacted with the mouse TLR9 and had no cross reactivity with human TLR9 (FIG. 7A).

Since it was important to determine whether the epitope of the above monoclonal antibodies was either TLR9N or TLR9C in consideration of protein cleavage of the ectodomain of TLR9 in DNA sensing, a cleavage site of TLR9 was determined first. TLR9-GFP expressed in M12B cell lymphoma was compared with that expressed in PRAT41 expression-suppressed M12 cells. The PRAT4A is a TLR-specific chaperon and TLR9 cannot go out from the endoplasmic reticulum in the absence of PRAT4A so that it is not subjected to processing. It was therefore presumed that a fragment not observed in the PRAT4A expression-suppressed M12 cells was very likely to TLR9C (FIG. 7B).

The TLR9C fragment detected was purified and its N-terminal amino acid sequence was determined. It has been found that TLR9C started from 461T or 467F (FIG. 7C). The cleavage site determined was a region between leucine-rich repeat 14 (LRR14) and LRR15 (FIG. 7D), which coincided with an expectation based on the past report. Presence of two kinds of N terminals is explained by successive processing of TLR9 with asparagine endopeptidase and cathepsin. According to these N-terminal amino acid sequences, chimeric proteins composed of an N-terminal HA epitope, TLR9 ectodomain, and membrane permeability domain were expressed in Ba/F3 cells. The cells thus established were stained with an anti-TLR antibody. Two monoclonal antibodies J15A7 and B33A4 reacted with TLR9N and C34A1 bound to TLR9C (FIG. 7E). Binding of J15A7 to TLR9N was much weaker than that to B33A4.

Expression of TLR9 in the Surface of Spleen-Derived DC

It has been thought that TLR9 is secreted from the cell surface, but expression of endogenous TLR9 in the surface of primary immune cells has not yet been reported. Expression of TLR9 in the cell surface was studied using an anti-TLR9 antibody.

First, excessive expression of TLR9 was caused in Ba/F3 cells. Then, as expected, no TLR9 was detected from the surface of the TLR9-expressed Ba/F3 cells and only TLR9 in the endosome was detected by membrane permeability staining (FIG. 8A, upper side). Unc93B1 transports TLR9 from the endoplasmic reticulum to the endolysosome. In consideration of the possibility of the Unc93B1 transporting TLR9 also to the cell surface, Unc93B1 was also excessively expressed in the Ba/F3 cells expressing TLR9. The J15A7 and C34A1 detected the cell surface TLR9, but did not detect B33A4, anti-TLR9N (bottom side, FIG. 8A). J15A7 detected the cell surface TLR9 also in the spleen-derived pDC, CD8α+ cDC, CD4+ cDC, and CD4-CD8-cDC. Specificity of J15A7 staining was confirmed by Tlr9$^{-/-}$DC. The cell surface TLR9 was not detected in DC derived from the spleen of Unc93b1$^{3d/3d}$ mice having, in the mouse Unc93B1 gene thereof, a function-lost type mutation. From the above results showing that excessive expression of Unc93B1 induces expression of the cell surface TLR9 in the Ba/F3 cells, it has been found that Unc93B1 plays an important role in transport of TLR9 to the cell surface.

Amino Acid Sequence Analysis of Antibody and CDR

The heavy chain amino acid sequence and the light chain amino acid sequence, each of the monoclonal antibody available from the hybridoma line J15A7 antibody are represented by SEQ ID NO: 29 and SEQ ID NO: 30, respectively. The amino acid sequences of the heavy chain CDRs 1 to 3 and the amino acid sequences of the light chain CDRs 1 to 3, each of the above antibody are represented by SEQ ID NOs: 11 to 13 and SEQ ID NOs: 14 to 16, respectively.

The heavy chain amino acid sequence and the light chain amino acid sequence, each of the monoclonal antibody available from the hybridoma line B33A4 antibody are represented by SEQ ID NO: 31 and SEQ ID NO: 32, respectively. The amino acid sequences of the heavy chain CDRs 1 to 3 and the amino acid sequences of the light chain CDRs 1 to 3, each of the above antibody are represented by SEQ ID NOs: 17 to 19 and SEQ ID NOs: 20 to 22, respectively.

The heavy chain amino acid sequence and the light chain amino acid sequence, each of the monoclonal antibody available from the hybridoma line C34A1 antibody are represented by SEQ ID NO: 33 and SEQ ID NO: 34, respectively. The amino acid sequences of the heavy chain CDRs 1 to 3 and the amino acid sequences of the light chain CDRs 1 to 3, each of the above antibody are represented by SEQ ID NOs: 23 to 25 and SEQ ID NOs: 26 to 28, respectively.

[Sequence Listing Free Text]

SEQ ID NO: 1 represents the amino acid sequence of mouse TLR7.

SEQ ID NO: 2 represents the amino acid sequence of mouse TLR9.

SEQ ID NO: 3 represents the amino acid sequence of heavy chain CDR1 of A94B10 antibody.

SEQ ID NO: 4 represents the amino acid sequence of heavy chain CDR2 of A94B10 antibody.

SEQ ID NO: 5 represents the amino acid sequence of heavy chain CDR3 of A94B10 antibody.

SEQ ID NO: 6 represents the amino acid sequence of light chain CDR1 of A94B10 antibody.

SEQ ID NO: 7 represents the amino acid sequence of light chain CDR2 of A94B10 antibody.

SEQ ID NO: 8 represents the amino acid sequence of light chain CDR3 of A94B10 antibody.

SEQ ID NO: 9 represents the amino acid sequence of a heavy chain of A94B10 antibody.

SEQ ID NO: 10 represents the amino acid sequence of a light chain of A94B10 antibody.

SEQ ID NO: 11 represents the amino acid sequence of heavy chain CDR1 of J15A7 antibody.

SEQ ID NO: 12 represents the amino acid sequence of heavy chain CDR2 of J15A7 antibody.

SEQ ID NO: 13 represents the amino acid sequence of heavy chain CDR3 of J15A7 antibody.

SEQ ID NO: 14 represents the amino acid sequence of light chain CDR1 of J15A7 antibody.

SEQ ID NO: 15 represents the amino acid sequence of light chain CDR2 of J15A7 antibody.

SEQ ID NO: 16 represents the amino acid sequence of light chain CDR3 of J15A7 antibody.
SEQ ID NO: 17 represents the amino acid sequence of heavy chain CDR1 of B33A4 antibody.
SEQ ID NO: 18 represents the amino acid sequence of heavy chain CDR2 of B33A4 antibody.
SEQ ID NO: 19 represents the amino acid sequence of heavy chain CDR3 of B33A4 antibody.
SEQ ID NO: 20 represents the amino acid sequence of light chain CDR1 of B33A4 antibody.
SEQ ID NO: 21 represents the amino acid sequence of light chain CDR2 of B33A4 antibody.
SEQ ID NO: 22 represents the amino acid sequence of light chain CDR3 of B33A4 antibody.
SEQ ID NO: 23 represents the amino acid sequence of heavy chain CDR1 of C34A1 antibody.
SEQ ID NO: 24 represents the amino acid sequence of heavy chain CDR2 of C34A1 antibody.
SEQ ID NO: 25 represents the amino acid sequence of heavy chain CDR3 of C34A1 antibody.
SEQ ID NO: 26 represents the amino acid sequence of light chain CDR1 of C34A1 antibody.
SEQ ID NO: 27 represents the amino acid sequence of light chain CDR2 of C34A1 antibody.
SEQ ID NO: 28 represents the amino acid sequence of light chain CDR3 of C34A1 antibody.
SEQ ID NO: 29 represents the amino acid sequence of a heavy chain of J15A7 antibody.
SEQ ID NO: 30 represents the amino acid sequence of a light chain of J15A7 antibody.
SEQ ID NO: 31 represents the amino acid sequence of a heavy chain of B33A4 antibody.
SEQ ID NO: 32 represents the amino acid sequence of a light chain of B33A4 antibody.
SEQ ID NO: 33 represents the amino acid sequence of a heavy chain of C34A1 antibody.
SEQ ID NO: 34 represents the amino acid sequence of to light chain of C34A1 antibody.
SEQ ID NO: 35 represents the DNA sequence of CpGB.
SEQ ID NO: 36 represents the DNA sequence of CpGA.
SEQ ID NO: 37 represents the RNA sequence of PolyU.
SEQ ID NO: 38 represents the RNA sequence of RNA9.2s-DR.
SEQ ID NO: 39 represents the amino acid sequence on human TLR7.

The invention claimed is:

1. An anti-TLR7-antibody (anti-Toll-like receptor 7) selected from the group consisting of:

(i) an antibody containing a heavy chain CDR1 having the amino acid sequence represented by SEQ ID NO: 3, a heavy chain CDR2 having the amino acid sequence represented by SEQ ID NO: 4, a heavy chain CDR3 having the amino acid sequence represented by SEQ ID NO: 5, a light chain CDR1 having the amino acid sequence represented by SEQ ID NO: 6, a light chain CDR2 having the amino acid sequence represented by SEQ ID NO: 7, and a light chain CDR3 having the amino acid sequence represented by SEQ ID NO: 8; and (ii) an antibody containing a heavy chain having the amino acid sequence represented by SEQ ID NO: 9 and a light chain having the amino acid sequence represented by SEQ ID NO: 10.

2. A method of treating a TLR7-dependent inflammatory disease comprising a step of administering a therapeutic agent to a subject, the therapeutic agent comprising an anti-TLR7 (anti-Toll-like receptor 7) antibody according to claim 1.

3. The method of treating the inflammatory disease according to claim 2, wherein the anti-TLR7 antibody is an antibody containing a heavy chain CDR1 having the amino acid sequence represented by SEQ ID NO: 3, a heavy chain CDR2 having the amino acid sequence represented by SEQ ID NO: 4, a heavy chain CDR3 having the amino acid sequence represented by SEQ ID NO: 5, a light chain CDR1 having the amino acid sequence represented by SEQ ID NO: 6, a light chain CDR2 having the amino acid sequence represented by SEQ ID NO: 7, and a light chain CDR3 having the amino acid sequence represented by SEQ ID NO: 8.

4. The method of treating the TLR7-dependent inflammatory disease according to claim 2, wherein the TLR7 antibody is an antibody containing a heavy chain having the amino acid sequence represented by SEQ ID NO: 9 and a light chain having the amino acid sequence represented by SEQ ID NO: 10.

5. The method of treating the TLR7-dependent inflammatory disease according to claim 2, wherein the TLR7-dependent inflammatory disease is an autoimmune disease.

6. The method of treating the TLR7-dependent inflammatory disease according to claim 5, wherein the autoimmune disease is systemic lupus erythematosus or psoriasis.

* * * * *